United States Patent
Manoharan et al.

(10) Patent No.: US 6,576,752 B1
(45) Date of Patent: *Jun. 10, 2003

(54) AMINOOXY FUNCTIONALIZED OLIGOMERS

(75) Inventors: Muthiah Manoharan, Carlsbad, CA (US); Harri Lonnberg, Turku (FI); Harri Salo, Turku (FI); Pasi Virta, Leito (FI)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,260

(22) Filed: Jun. 25, 1999

Related U.S. Application Data

(63) Continuation-in-part of application No. 09/016,520, filed on Jan. 30, 1998, now Pat. No. 6,127,533.
(60) Provisional application No. 60/037,143, filed on Feb. 14, 1997.

(51) Int. Cl.[7] .................. C07H 21/00; C07H 21/02; C07H 21/04
(52) U.S. Cl. .................. 536/23.2; 536/25.31; 435/6; 435/7.94
(58) Field of Search ................ 536/23.2, 25.31; 455/6, 7.94

(56) References Cited

U.S. PATENT DOCUMENTS

| | | | |
|---|---|---|---|
| 3,687,808 A | 8/1972 | Merigan et al. | 195/28 |
| 4,469,863 A | 9/1984 | Ts'o et al. | 536/27 |
| 5,013,830 A | 5/1991 | Ohtsuka et al. | 536/27 |
| 5,034,506 A | 7/1991 | Summerton et al. | 528/391 |
| 5,138,045 A | 8/1992 | Cook et al. | 536/27 |
| 5,166,195 A | 11/1992 | Ecker | 514/44 |
| 5,166,197 A * | 11/1992 | Cook et al. | 536/23.1 |
| 5,202,211 A | 4/1993 | Imai et al. | |
| 5,210,264 A | 5/1993 | Yau | 558/167 |
| 5,214,134 A | 5/1993 | Weis et al. | 536/25.3 |
| 5,218,105 A | 6/1993 | Cook et al. | 536/25.31 |
| 5,223,618 A * | 6/1993 | Cook et al. | 544/276 |
| 5,242,906 A | 9/1993 | Pagano et al. | 514/44 |
| 5,248,670 A | 9/1993 | Draper et al. | 514/44 |
| 5,264,562 A * | 11/1993 | Matteucci et al. | 536/23.1 |
| 5,278,302 A | 1/1994 | Caruthers et al. | 536/24.5 |
| 5,321,131 A | 6/1994 | Agrawal et al. | 536/25.34 |
| 5,359,044 A | 10/1994 | Cook et al. | 536/23.1 |
| 5,359,051 A | 10/1994 | Cook et al. | 536/26.7 |
| 5,378,825 A * | 1/1995 | Cook et al. | 536/25.34 |
| 5,386,023 A | 1/1995 | Sanghvi et al. | 536/25.3 |
| 5,430,136 A | 7/1995 | Urdea et al. | 536/243 |
| 5,434,257 A | 7/1995 | Matteucci et al. | 536/24.3 |
| 5,442,049 A | 8/1995 | Anderson et al. | 536/24.5 |
| 5,455,233 A | 10/1995 | Spielvogel et al. | 514/44 |
| 5,457,189 A | 10/1995 | Crooke et al. | 536/24.5 |
| 5,457,191 A | 10/1995 | Cook et al. | 536/27.13 |
| 5,459,255 A | 10/1995 | Cook et al. | 536/27.13 |
| 5,464,746 A | 11/1995 | Fino | 435/6 |
| 5,466,677 A | 11/1995 | Baxter et al. | 514/44 |

(List continued on next page.)

FOREIGN PATENT DOCUMENTS

| | | |
|---|---|---|
| EP | 216 860 | 3/1986 |
| EP | 260032 | 8/1987 |
| EP | 399842 | 4/1989 |
| EP | 399330 | 5/1990 |
| WO | WO 89/12060 | 12/1989 |
| WO | WO 90/15065 | 12/1990 |
| WO | WO 91/06556 | 6/1991 |
| WO | WO 91/08213 | 6/1991 |
| WO | WO 91/10671 | 7/1991 |
| WO | WO 91/15499 | 10/1991 |
| WO | WO 91/15500 | 10/1991 |
| WO | WO 91/18997 | 12/1991 |
| WO | WO 92/02258 | 2/1992 |
| WO | WO 92/03464 | 3/1992 |
| WO | WO 92/03568 | 3/1992 |
| WO | 9203732 | 3/1992 |
| WO | WO 92/05186 | 4/1992 |
| WO | WO 93/07883 | 10/1992 |
| WO | WO 92/19637 | 11/1992 |
| WO | WO 92/20822 | 11/1992 |
| WO | WO 92/20823 | 11/1992 |
| WO | WO 92/22651 | 12/1992 |
| WO | 9306925 | 4/1993 |
| WO | 9830575 | 7/1993 |
| WO | 9322680 | 11/1993 |
| WO | WO 94/02501 | 2/1994 |
| WO | 9402501 | * 2/1994 |
| WO | 9639531 | * 12/1996 |
| WO | 9835978 | * 8/1998 |

OTHER PUBLICATIONS

Loakes et al., "Antiviral Activity of Bicyclic Pyrimidine Nucleosides," *Antiviral Chemistry and Chemotherapy*, 6(6), 371–378 (1995). Month of publication data is unavailable.*

Takaku, H. et al., "Synthesis of Oligoribonucleotides Using 4–Methoxybenzyl Group as a New Protecting Group of the 2'–Hydroxyl Group of Adenosine", *Chemistry Letts.*, 1982, 189–192.

Vasseur, J.J. et al., "Oligonucleosides: Synthesis of a Novel Methylhydroxylamine–linked Nucleoside Dimer and Its Incorporation into Antisense Sequences", *J. Am. Chem. Soc.*, 1992, 114, 4006–4007.

(List continued on next page.)

*Primary Examiner*—Johann Richter
*Assistant Examiner*—L. E. Crane
(74) *Attorney, Agent, or Firm*—Woodcock Washburn LLP

(57) ABSTRACT

The present invention provides oligomers which are specifically hybridizable with a selected sequence of RNA or DNA wherein at least one of the nucleoside moieties of the oligomer is modified to include an aminooxy linkage. These oligomers are useful for diagnostic, therapeutic and investigative purposes.

18 Claims, 15 Drawing Sheets

U.S. PATENT DOCUMENTS

| | | | |
|---|---|---|---|
| 5,466,786 A | 11/1995 | Buhr et al. | 536/26.26 |
| 5,470,967 A | 11/1995 | Huie et al. | 536/24.3 |
| 5,489,677 A | 2/1996 | Sanghvi et al. | 536/22.1 |
| 5,506,351 A | 4/1996 | McGee | 536/55.3 |
| 5,510,239 A | 4/1996 | Baracchini, Jr. et al. | 435/6 |
| 5,510,476 A | 4/1996 | Ravikumar et al. | 536/25.31 |
| 5,512,329 A | 4/1996 | Guire et al. | |
| 5,514,577 A | 5/1996 | Draper et al. | 435/238 |
| 5,514,786 A | 5/1996 | Cook et al. | 536/23.1 |
| 5,514,788 A | 5/1996 | Bennett et al. | 536/23.1 |
| 5,519,126 A | 5/1996 | Hecht | 536/24.3 |
| 5,523,389 A | 6/1996 | Ecker et al. | 536/23.1 |
| 5,541,307 A | 7/1996 | Cook et al. | 536/23.1 |
| 5,543,507 A | 8/1996 | Cook et al. | 536/23.1 |
| 5,563,056 A | 10/1996 | Swan et al. | |
| 5,563,255 A | 10/1996 | Monia et al. | 536/24.31 |
| 5,571,902 A * | 11/1996 | Ravikumar et al. | 536/22.1 |
| 5,576,208 A | 11/1996 | Mornia et al. | 435/240.2 |
| 5,576,302 A | 11/1996 | Cooke et al. | 514/44 |
| 5,578,718 A * | 11/1996 | Cook et al. | 536/27.21 |
| 5,580,767 A | 12/1996 | Cowsert et al. | 435/172.3 |
| 5,582,972 A | 12/1996 | Lima et al. | 435/6 |
| 5,582,986 A | 12/1996 | Monia et al. | 435/6 |
| 5,587,361 A | 12/1996 | Cook et al. | 514/44 |
| 5,587,469 A | 12/1996 | Cook et al. | 536/23.1 |
| 5,591,600 A | 1/1997 | Ecker | 435/69.1 |
| 5,591,623 A | 1/1997 | Bennett et al. | 435/240.2 |
| 5,591,720 A | 1/1997 | Anderson et al. | 514/44 |
| 5,596,086 A * | 1/1997 | Matteucci et al. | 536/22.1 |
| 5,670,633 A | 9/1997 | Cook et al. | 536/23.1 |
| 5,681,940 A | 10/1997 | Wang et al. | 536/22.1 |
| 5,707,813 A | 1/1998 | Dandliker et al. | |
| 5,736,257 A | 4/1998 | Conrad et al. | |
| 5,741,551 A | 4/1998 | Guire et al. | |
| 5,792,608 A * | 8/1998 | Swaminathan et al. | 435/6 |
| 5,817,781 A * | 10/1998 | Swaminathan et al. | 536/22.1 |
| 5,985,663 A * | 11/1999 | Bennett et al. | 435/375 |
| 6,127,533 A * | 10/2000 | Cook et al. | 536/23.1 |
| 6,172,209 B1 * | 1/2001 | Manoharan et al. | 536/23.1 |
| 6,271,358 B1 * | 8/2001 | Manoharan et al. | 536/23.1 |

* cited by examiner

OTHER PUBLICATIONS

Wang, H. et al., "Solid Phase Synthesis of Neutral Oligonucleotide Analogues", Tetrahedron Letts., 1991, 32 7385–7388.

Yano, J. et al., "A Simple Method of the Preparation of 2'–O–Methyladenosine", Biochim. Biophys. Acta, 1980, 629, 178–183.

Zhang, Z. et al., "Uptake of N–(4'–pyridoxyl)amines and release of amines by renal cells: A model for transporter–enhanced delivery of bioactive compounds", Proc. Natl. Acad. Sci., 1991, 88, 10407–10410.

Zhong, Y.L. et al., "Efficient and Facile Glycol Cleavage Oxidation Using Improved Silica Gel–Supported Sodium Metaperiodate", J. Org. Chem., 1997, 62, 2622–2624.

Agrawal et al. (eds.), "Methods of Molecular Biology", in Protocols for Oligonucleotide Conjugates, Agrawal, S. (ed.), Humana Press, New Jersey, 1994, vol. 26, 1–72. Month of publication data is unavailable for this reference.

Albert, P.R. et al., "Antisense knockouts: molecular scalpels for the dissection of signal transduction", Trends Pharmacol. Sci., 1994, 15, 250–254 (Jul., 1998).

Albretsen, C. et al., "Applications of Magnetic Beads with Covalently Attached Oligonucleotides in Hybridization: Isolation and Detection of Specific Measles Virus mRNA from a Crude Cell Lysate," Anal. Biochem., 1990, 189, 40–50. Month of publication data is unavailable.

Azhayev, A. et al., "Analogues of Oligonucleotides Containing 3'–Deoxy–β–Psicothymidine," Tetra. Lett., 1993, 34(40), 6435–6438. Month of publication data is unavailable.

Beaucage, S.L. et al., "Advances in the Synthesis of Oligonucleotides by the Phosphoramidite Approach", Tetrahedron, 1992, 48, 2223–2311. Month of publication data is unavailable for this reference.

Bischoff, R. et al., "Introduction of 5'–Terminal Functional Groups into Synthetic Oligonucleotides for selective Immobilization", Analyt. Biochem., 1987, 164, 336–344. Month of publication data is unavailable for this reference.

Chee, M. et al., "Accessing Genetic Information with High–Density DNA Arrays," Science, 1996, 274, 610–614 (Oct. 25, 1996). Month of publication data is unavailable for this reference.

Cohen, G. et al., "Covalent attachment of DNA oligonucleotides to glass," Nucl. Acids Res., 1997, 25(4), 911. Month of publication data is unavailable for this reference.

Cook, P.D., "Medicinal Chemistry of Antisense Oligonucleotides—future opportunities", Anti–Cancer Drug Design, 1991, 6, 585–607. Month of publication data is unavailable for this reference.

Cronin, M.T. et al., "Cystic Fibrosis Mutation Detection by Hybridization to Light–Generated DNA Probe Arrays," Human Mat., 1996, 7, 244–255. Month of publication data is unavailable for this reference.

Damha, M.J. et al., "An improved procedure for derivatization of controlled–pore glass beads for solid–phase oligonucleotides synthesis," Nucl. Acids Res., 1990, 18(13), 3813–3821. Month of publication data is unavailable for this reference.

Delgado, C. et al., "The Uses and Properties of PEG–Linked Proteins", Crit. Rev. in Therapeutic Drug Carrier Sys., 1992, 9, 249–304. Month of publication data is unavailable for this reference.

Ducray, P. et al., "Enantioconvergent Formal Synthesis of Brefeldin A via Sakai–Catalyzed Cyclization," J. Org. Chem., 1999, 64, 3800–3801 (issue #11). Month of publication data is unavailable for this reference.

Englisch, U. et al., "Chemically Modified Oligonucleotides as Probes and Inhibitors", Angew. Chem. Int. Ed. Eng., 1991, 30, 613–629 (Jun., 1991). Month of publication data is unavailable for this reference.

Erout, M–N. et al., "Preparation of Conjugates between Oligonucleotides and N–Vinylpyrrolidone/N–Acryloxysuccinimide Copolymers and Applications in Nucleic Acid Assays to Improve Sensitivity," Bioconjugate Chem., 1996, 7, 568–575 (Issue #5). Month of publication data is unavailable for this reference.

Hovinen, J. et al., "Novel Solid Supports for the Preparation of 3'–Derivatized Oligonucleotides: Introduction of 3'–Alkylphosphate Tether Groups Bearing Amino, Carboxy, Carboxamido, and Mercapto Fuctionalities," Tetrahedron, 1994, 50, 7203–7218 (issue #24). Month of publication data is unavailable for this reference.

Kawasaki, A.M. et al., "Synthesis, Hybridization, and Nuclease Resistance Properties of 2'–O–Aminooxyethyl (2'–O–AOE) Modified Oligonucleotides," *Tetra. Lett.,* 1999, 40, 661–664. Month of publication data is unavailable for this reference.

Kozal, M.J. et al., "Extensivie polymorphisms observed in HIV–1 clade B protease gene using high–density oligonucleotide arrays," *Nat. Med.,* 1996, 2(7), 753–759 (Jul., 1996). Month of publication data is unavailable for this reference.

Kremsky, J.N. et al., "Immobilization of DNA via oligonucleotides containing an aldehyde or carboxylic acid group at the 5'terminus," *Nucl. Acids Res.,* 1987, 15(7), 2891–2909. Month of publication data is unavailable for this reference.

Kroschwitz, J.I., "Polynucleotides", Concise Encyclopedia of Polymer Science and Engineering, 1990, John Wiley & Sons, New York, 858–859. Month of publication data is unavailable for this reference.

Kung, P–P. et al., "One–Flask Syntheses of 6–Thioguanosine and 2'–Deoxy–6–Thioguanosine," *Tetra. Lett.,* 1991, 32(32), 3919–3922. Month of publication data is unavailable for this reference.

Kwoh, D.Y. et al., "Transcription–based amplification system ad detection of amplified human immunodeficiency virus type 1 with a bead–based sandwich hybridization format," *Proc. Natl. Acac. Sci. USA,* 1989, 86, 1173–1177 (Feb., 1989).

Lamture, J.B. et al., "Direct detection of nucleic acid hybridization on the surface of a charge coupled device," *Nucl. Acids Res.,* 1994, 22(11), 2121–2125. Month of publication data is unavailable for this reference.

Lemieux, G.A. et al., "Exploiting Differences in Sialoside Expression for Selective Targeting of MRI Contrast Reagents," *J. Am. Chem. Soc.,* 1999, 121, 4278–4279 (issue #17). Month of publication data is unavailable for this reference.

Lövgren, T. et al., "Sensitive bioaffinity assays with individual microparticles and time–resolved fluorometry," *Clin. Chem.,* 1997, 43(10), 1937–1943. Month of publication data is unavailable for this reference.

Lund, V. et al., "Assessment of methods for covalent binding of nucleic acids to magnetic beads, Dynabeads™, and the characteristics of the bound nucleic acids in hybridization reactions", *Nucl. Acids Res.,* 1988, 16, 10861–10880 (issue #22). Month of publication data is unavailable for this reference.

Maskos, U. et al., "Oligonucleotide hybridisations on glass supports: a novel linker for oligonucleotide synthesis and hybridisation properties of oligonucleotides synthesised in situ", *Nucl. Acids Res.,* 1992, 20, 1679–1684 (issue #7). Month of publication data unavailable for this reference.

Mitsunobu,O., "The Use of Diethyl Azodicarboxylate and Triphenylphosphine in Synthesis and Transformation of Natural Products," *Synthesis,* 1981, 1–28 (Jan., 1991). Month of publication data is unavailable for this reference.

Mukkala, V–M. et al., "85. Development of Luminescent Europium(III) and Terbium(III) Chelates of 2,2':6'2"–Terpyridine Derivatives for Protein Labelling," *Helv. Chim. Acta.,* 1993, 76, 1361–1378. Month of publication data is unavailable for this reference.

O'Donnell, M.J. et al., "High–Density, Covalent Attachement of DNA to Silicon Waferes for Analysis by Malde–TOF Mass Spectrometry," *Anal. Chem.,* 1997, 69, 2438–2433 (Jul. 1, 1997).

Ouchi, T. et al., "Synthesis and Antitumor Activity of Poly(Ethylene Glycols)s Linked to 5'–Fluorouracil via a Urethane or Urea Bond", *Drug Des. & Disc.,* 1992, 9, 93–105. Month of publication data is unavailable for this reference.

Pirrung, M.C. et al., "Comparison of Methods for Photochemical Phosphoramidite–Based DNA Synthesis," *J. Org. Chem.,* 1995, 60, 6270–6276 (issue #20). Month of publication data is unavailable for this reference.

Polushin, N. N. et al., "Synthesis of Oligonucleotides Containing 2'–Azido–and 2'Amino–2'–deoxyuridine Using Phosphotriester Chemistry," *Tetrahedron Letts.,* 1996, 37(19), 3227–3230. Month of publication data is unavailable for this reference.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.,* 1991, 56, 4329–4333 (issue #13). Month of publication data is unavailable for this reference.

Saiki, R.K. et al., "Genetic analysis of amplified DNA with immobilized sequence–specific oligonucleotide probes," *Proc. Natl. Acad. Sci. USA,* 1989, 86, 6230–6234 (Aug., 1989).

Southern, E.M. et al., "Discovering antisense reagents by hybridization of RNA to oligonucleotide arrays," in *Oligonucleotides as Therapeutic Agents,* Ciba Foundation Symposium, 1997, 209, 38–46. Month of publication data is unavailable for this reference.

Tang, K. et al., "Matrix–assisted lasere desorption/ionizaiton mass spectrometry of immobilized duplex DNA probes," *Nucl. Acids Res.,* 1995, 23(16), 3126–3131. Month of publication data is unavailable for this reference.

Thomson, J. B. et al., "Synthesis and Properties of Diuridine Phosphate Analogues Containing Thio and Amino Modifications," *J. Org. Chem.,* 1996, 61, 6273–6281 (issue #18). Month of publication data is unavailable for this reference.

Timofeev, E.N. et al., "Regioselective immobilizaiton of short oligonucleotides to acrylic copolymer gels," *Nucl. Acid Res.,* 1996, 24(16), 3142–3148 (Issue #16). Month of publication data is unavailable for this reference.

Van Ness, J. et al., "A versatile solid support system for oligodeoxynucleotide probe–based hybridization assays", *Nucl. Acids Res.,* 1991, 19, 3345–3350 (Issue #12). Month of publication data is unavailable for this reference.

Williams,M.A. et al., "Synthesis of Enantiomerically Pure Diethylenetriaminepentaacetic Acid Analogues. L–Phenylalanine as the Educt for Substitution at the Central Acetic Acid," *J. Org. Chem.,* 1993, 58, 1151–1158 (Issue #5). Month of publication data is unavailable for this reference.

Yarden, R.I. et al., "BRCA1 interacts with components of the histone deacetylase complex," *Proc. Natl. Acad. Sci. USA,* 1999, 96, 4938–4988 (Apr., 1999).

Yershov, G. et al., "DNA analysis and diagnostics on oligonucleotide microchips," *Proc. Natl. Acad. Sci USA,* 1996, 93, 4913–4918 (May, 1996).

Zhang et al., "Single–base mutational analysis of cancer and genetic diseases using membrane bound modified oligonucleotides," *Nucl. Acids Res.,* 1991, 19(14), 3929–3933. Month of publication data is unavailable for this reference.

Arnott, S. et al., "Optimized Parameters for A–DNA and B–DNA", *Biochem. Biophys. Res. Comm.*, 1972, 47, 1504–1510.

Beaucage, S.L. et al., "Deoxynucleoside Phosphoramidites–A New Class of Key Intermediates for Deoxypoylnucleotide Synthesis", *Tetrahedron Letts.*, 1981, 22, 1859–1862.

Caruthers, M.H., "Synthesis of Oligonucleotides and Oligonucleotide Analogues", *Oligonucleotides: Antisense Inhibitors of Gene Expression*, 1989 Chapter 1, Cohen, J.S. (Ed.), CRC Press, Boca Raton, FL, 7–24.

Christensen, L.F. et al., "Specific Chemical Synthesis of Ribonucleoside O–Benzyl Ethers", *J. Org. Chem.*, 1972, 37, 3398–3401.

Coull, J.M. et al., "Synthesis and characterization of a Carbamate–Linked Oligonucleoside", *Tetrahedron Letts.*, 1987, 28, 745–748.

Gryaznov, S. et al., "Stabilization of DNA:RNA Duplexes by Substitution of 2'–deoxyadenosine with 2'–deoxy2–aminoadenosine", *Tetrahedron Lett.*, 1994, 35, 2489–2492.

Guinosso, C.J. et al., "Synthesis and Biophysical and Biological Evaluation of 2'–Modified Antisense Oligonucleotides", *Nucleosides & Nucleotides*, 1991, 10, 259–262.

Guschlbauer, W. et al., "Nucleoside conformation is determined by the electronegativity of the sugar substituent", *Nuc. Acids. Res.*, 1980, 8, 1421–1433.

Hewitt, J.M. et al., "Structural Determination of Silicon–Containing Oligonucleotides by $^1H-^{29}Si$ Long–Range Heteronuclear Multiple Quantum Correlation NMR Spectroscopy", 1992, 11, 1661–1666.

Hobbs, J. et al., "Polynucleotides Containing 2'Chloro–2'–deoxyribose", *Biochemistry*, 1972, 11, 4336–4344.

Ikehara, M. et al., "Polynucleotides. LVI. Synthesis and properties of poly(2'–deoxy–2'–fluoroinosinic acid)", *Nuc. Acids Res.*, 1978, 5, 3315–3325.

Ikehara, M. et al., "Polynucleotides. L. Synthesis and properties of poly(2'–chloro–2'–deoxyadenylic acid) and poly(2'–bromo–2'deoxyadenylic acid)", *Nuc. Acids Res.*, 1977, 4, 4249–4260.

Inoue, H. et al., "Synthesis and hybridixation studies on two complementary nona(2'–O–methyl) ribonucleotides", *Nuc. Acids Res.*, 1987, 15, 6131–6148.

Iyer, R.P., "3H–1,2–Benzodithiole–3one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Izatt, R.M. et al., "Proton Ionization from Adenosine", *J. Am. Chem. Soc.*, 1965, 87, 2760–2761.

Krolikiewicz, K. et al., "The Synthesis of 2–Fluoropurine Nucleosides", *Nucleosides & Nucleotides*, 1994, 13, 673–678.

Manoharan, M. et al., "Novel Functionalization of the Sugar Moiety of Nucleic Acids for Multiple Labeling in the Minor Groove", *Tetrahedron Letts.*, 1991, 32, 7171–7174.

Martin, P., "Ein neuer Zugang zu 2'–O–Alkylribonucleosiden und Eigenschaften deren Oligonucleotide", *Helvetica Chimica Acta*, 1995, 78, 486–504 (*English summary included*).

Mertes, M.P. et al., "Synthesis of Carbonate Analogs of Dinucleosides. 3'–Thymidinyl 5'–Thymidinyl Carbonate, 3'–Thymidinyl 5'–(5–Fluoro–2'–deoxyuridinyl) Carbonate, and 3'–(5–Fluoro–2'–deoxyuridinyl) 5'–Thymidinyl Carbonate", *J. Med. Chem.*, 1969, 12, 154–157.

Mungall, W.S. et al., "Carbamate Analogues of Oligonucleotides", *J. Org. Chem.*, 1977, 42, 703–706.

Musicki, B. et al., "Synthesis of Carbohydrate Sulfonates and Sulfornate Esters", *J. Org. Chem.*, 1990, 55, 4231–4233.

Ohtsuka, E. et al., "Recognition by restriction endonuclease *Eco*RI of deoxyoctanucleotides containing modified sugar moieties", *European J. Biochem.*, 1984, 139, 447–450.

Reynolds, R.C. et al., "Synthesis of Thymidine Dimers Containing Internucleoside Sulfonate and Sulfonamide Linkages", *J. Org. Chem.*, 1992, 57, 2983–2985.

Sambrook, J. et al., "Labeling of Synthetic oligonucleotides by Phosphorylation with Bacteriophage T4 Polynucleotide Kinase", *Molecular Cloning. A Laboratory Manual*, 1989, vol. 2, Cold Spring Harbor Laboratory Press, 11.31–11.32.

Shibahara, S. et al., "Inhibition of human immunodeficiency virus (HIV–I) replication by synthetic oligo–RNA derivatives", *Nuc. Acids. Res.*, 1989, 17, 239–252.

Sood, A. et al., "Boron–Containing Nucleic Acids. 2. Synthesis of Oligodeoxynucleoside Boranophosphates", *J. Am. Chem. Soc.*, 1990, 112, 9000–9001.

Stirchak, E. P. et al., "Uncharged Stereoregular Nuclic Acid Analogs. I. Synthesis of a Cytosine–Containing Oligomer with Carbamate Internucleoside Linkages", *J. Org. Chem.*, 1987, 52, 4202–4206.

Stirchak, E.P. et al., "Uncharged Stereoregular nuclic acid analogs: 2. Morpholino nucleoside oligomer with carbamate internucleoside linkages", *Nuc. Acid. Res.*, 1989, 17, 6129–6134.

Fahy, E. et al., "Design and synthesis of polyacrylamide–based oligonucleotide supports for use in nucleic acid diagnosis", *Nuc. Acids. Res.*, 1993, 21, 1819–1826 (issue #8). Month of publication data is unavailable for this reference.

Ghosh, S.S. et al., "Covalent attachment of oligonucleotides to solid supports", *Nucl. Acids Res.*, 1987, 15, 5353–5373 (issue #13). Month of publication data is unavailable for this reference.

Gibson, U.E.M. et al., "A Novel Method for Real Time Quantitive RT–PCR," *Genome Res.*, 1996, 6, 995–1001. Month of publication data is unavailable for this reference.

Glasser, "ISIS Pharmaceuticals Demonstrates Efficacy in Crohn's Disease with its Antisense Drug," *Genetic Eng. News*, 1997, 17, 1 and 34 (Mar. 1, 1997).

Guo, Z. et al., "Direct fluorescence analysis of genetic polymorphisms by hybridization with oligonucleotide arrays on glass supports", *Nucl. Acids Res.*, 1994, 22, 5456–5465 (issue #24). Month of publication data is unavailable for this reference.

Hacia, J.G. et al., "Two color hybridization analysis using high density oligonucleotide arrays and energy transfer dyes," *Nucl. Acids Res.*, 1998, 26(16), 3865–3866. Month of publication data is unavailable for this reference.

Hakala, H. et al., "Detection of Oligonucleotide Hybridization on a Single Microparticle by Time–Resolved Fluorometry: Quantitation and Optimization of a Sandwich Type Assay," *Bioconjugate Chem.*, 1998, 9, 316–321 (issue #3). Month of publication data is unavailable for this reference.

Hakala, H. et al., "Time–Resolved Fluorescence Detection of Oligonucleotide Hybridization on a Single Microparticle: Covalent Immobilization of Oligonucleotides and Quantitation of a Model System," *Bioconjugate Chem.*, 1997, 8, 232–237 (issue #2). Month of publication data is unavailable for this reference.

Hakala, H. et al., "Detection of Oligonucleotide Hybridization on a Single Microparticle by Time–Resolved Fluorometry: Hybridization Assays on Polymer Particles Obtained by Direct Solid Phase Assembly of the Oligonucleotide Probes," *Bioconjugate Chem.*, 1997, 8, 378–384 (issue #3). Month of publication data is unavailable for this reference.

Hamm, M. L. et al., "Incorporation of 2'–Deoxy–2–mercaptocytidine into Oligonucleotides via Phosphoramidite Chemistry," *J. Org. Chem.*, 1997, 62, 3415–3420 (issue #10). Month of publication data is unavailable for this reference.

i: DMTrCl/dioxane/Pyr;

ii: N-Hydroxyphthalimide/Ph₃P/DEAD/THF;

iii: dichloroacetic acid/CH₂Cl₂/MeOH;

iv: 2-cyanoethyl-$N,N,N',N'$-tetraisopropylphosphorodiamidite/1-$H$-tetrazole/MeCN.

i: TMSCl/Pyr/BzCl; ii: DMTrCl/Pyr; iii: 5-amino-
pentanol/TBD/I-PrOH; iv: N-Hydroxyphthalimide/Ph$_3$P/DEAD/THF;
v: 2-cyanoethyl-N,N,N',N'-
tetraisopropylphosphorodiamidite/1-H-tetrazole/MeCN; TBD:
1,5,7-triazabicyclo[4.4.0]dec-5-ene.

9: 5'-d(NH₂O-TEG-ACACCAAAGATGATAT)-3'

10: 5'-d[ACACCAAAGATGATATmC(ONH₂)T]-3'

TEG: tetraethylene glycol mC: N⁴-(5-hydroxypentyl)-2'-deoxycytidine i: Hydrazinium hydrate/Pyr/AcOH (0.124/4/1);

ii: RCHO in DMF or MeCN; iii: $NH_3$(aq).

3

Biotin-aminohexanal

18a
18b

19a
19b a, R = pyrenyl
b, R = retinolyl

AMINOOXY FUNCTIONALIZED OLIGOMERS

CROSS-REFERENCE TO RELATED APPLICATIONS

This patent application is a continuation-in-part application of U.S. application Ser. No. 09/016,520, filed on Jan. 30, 1998 now U.S. Pat. No. 6,127,533, which claims priority benefit of U.S. Provisional Application Serial No. 60/037,143, filed on Feb. 14, 1997.

FIELD OF THE INVENTION

The present invention relates to oligomers containing aminooxy linkages and methods of using such oligomers. More particularly, the oligomers of the present invention are used for investigative and therapeutic purposes.

BACKGROUND OF THE INVENTION

It has been recognized that oligonucleotides can be used to modulate mRNA expression by a mechanism that involves the complementary hybridization of relatively short oligonucleotides to mRNA such that the normal, essential functions of these intracellular nucleic acids are disrupted. Hybridization is the sequence-specific base pair hydrogen bonding of an oligonucleotide to a complementary RNA or DNA.

For use in diagnostics, and as research reagents and as therapeutics, the ability of an oligonucleotide to bind to a specific DNA or RNA with fidelity is an important factor. The relative ability of an oligonucleotide to bind to complementary nucleic acids is compared by determining the melting temperature of a particular hybridization complex. The melting temperature ($T_m$), a characteristic physical property of double helices, is the temperature (in °C.) at which 50% helical versus coil (unhybridized) forms are present. $T_m$ is measured by using UV spectroscopy to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the nucleic acid strands. Therefore, oligonucleotides modified to hybridize with appropriate strength and fidelity to its targeted RNA (or DNA) are greatly desired for use as research reagents, diagnostic agents and as oligonucleotide therapeutics.

Various substitutions have been introduced in the base and sugar moieties of the nucleosides of oligonucleotides. The inclusion of certain of these substitutions has resulted in improvements in the resulting oligonucleotide. One such useful improvement is an increase in the nuclease resistance of the oligonucleotides by the introduction of 2'-substituents such as alkoxy, allyloxy, and aminoalkyl groups.

Ikehara et al. (*European J. Biochem.*, 1984, 139, 447) have reported the synthesis of a mixed octamer containing one 2'-deoxy-2'-fluoroguanosine residue or one 2'-deoxy-2'-fluoroadenine residue. Guschlbauer and Jankowski (*Nucleic Acids Res*, 1980, 8, 1421) have shown that the contribution of the 3'-endo increases with increasing electronegativity of the 2'-substituent. Thus, 2'-deoxy-2'-fluorouridine contains 85% of the C3'-endo conformer.

Furthermore, evidence has been presented which indicates that 2'-substituted-2'-deoxyadenosine polynucleotides resemble double-stranded RNA rather than DNA. Ikehara et al. (*Nucleic Acids Res.*, 1978, 5, 3315) have shown that a 2'-fluoro substituent in poly A, poly I, or poly C duplexed to its complement is significantly more stable than the ribonucleotide or deoxyribonucleotide poly duplex as determined by standard melting assays. Ikehara et al. (*Nucleic Acids Res.*, 1978, 4, 4249) have shown that a 2'-chloro or bromo substituent in poly(2'-deoxyadenylic acid) provides nuclease resistance. Eckstein et al. (*Biochemistry*, 1972, 11, 4336) have reported that poly(2'-chloro-2'-deoxy-uridylic acid) and poly(2'-chloro-2'-deoxycytidylic acid) are resistant to various nucleases. Inoue et al. (*Nucleic Acids Res.*, 1987, 15, 6131) have described the synthesis of mixed oligonucleotide sequences containing 2'-OMe substituents on every nucleotide. The mixed 2'-OMe-substituted oligonucleotide hybridized to its RNA complement as strongly as the RNA-RNA duplex which is significantly stronger than the same sequence RNA-DNA heteroduplex ($T_m$s, 49.0 and 50.1 versus 33.0 degrees for nonamers). Shibahara et al. (*Nucleic Acids Res.*, 1987, 17, 239) have reported the synthesis of mixed oligonucleotides containing 2'-OMe substituents on every nucleotide. The mixed 2'-OMe-substituted oligonucleotides were designed to inhibit HIV replication.

It is believed that the composite of the hydroxyl group's steric effect, its hydrogen bonding capabilities, and its electronegativity versus the properties of the hydrogen atom is responsible for the gross structural difference between RNA and DNA. Thermal melting studies indicate that the order of duplex stability (hybridization) of 2'-methoxy oligonucleotides is in the order of RNA-RNA>RNA-DNA>DNA-DNA.

U.S. Pat. No. 5,013,830, issued May 7, 1991, discloses mixed oligonucleotides comprising an RNA portion, bearing 2'-O-alkyl substituents, conjugated to a DNA portion via a phosphodiester linkage. However, being phosphodiesters, these oligonucleotides are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. This application also discloses 2'-O-methyl phosphodiester oligonucleotides which lack nuclease resistance.

European Patent application 260,032, filed Aug. 27, 1987, discloses oligonucleotides having 2'-O-methyl substituents on the sugar moiety. This application also makes mention of other 2'-O-alkyl substituents, such as ethyl, propyl and butyl groups.

International Publication Number WO 91/06556, published May 16, 1991, and U.S. Pat. No. 5,466,786 discloses oligomers derivatized at the 2' position with substituents, which are stable to nuclease activity. Specific 2'-O-substituents which were incorporated into oligonucleotides include ethoxycarbonylmethyl (ester form), and its acid, amide and substituted amide forms.

European Patent application 399,330, filed May 15, 1990, discloses nucleotides having 2'-O-alkyl substituents.

International Publication Number WO 91/15499, published Oct. 17, 1991, discloses oligonucleotides bearing 2'-O-alkyl, -alkenyl and -alkynyl substituents.

Martin discloses certain nucleosides and oligonucleotides prepared therefrom that include 2'-methoxyethoxy, 2'-methoxy(tris-ethoxy) and other substituents. *Helvetica Chimica Acta*, 78, 1995, 486–504. Oligonucleotides containing nucleoside substituted with either the 2'-methoxyethoxy and 2'-methoxy(tris-ethoxy)substituents exhibited improved hybridization as judged by increase in Tm.

The expanding use of mixed-phase hybridization assays for the detection of specific nucleic acid sequences has made covalent immobilization of oligonucleotides to solid supports an object of increasing interest. See, Lund et al., *Nucleic Acids Res.*, 1988, 16, 10861; Saiki et al., *Proc. Natl. Acad. Sci. U.S.A.*, 1989, 86, 6230; Albretsen et al., *Anal. Biochem.*, 1990, 189, 40; Erout et al., *Bioconjugate Chem.*, 1996, 7, 568; Yershov et al., *Proc. Natl. Acad. Sci. U.S.A.*, 1996, 93, 4913; and Hakala et al., *Bioconjugate Chem.*, 1998, 9, 316.) Although the oligonucleotide probes may be assembled in situ on the support employed in the assay (Maskos and Southern, *Nucleic Acids Research*, 1992, 20, 1679; Pirrung and Bradley, *J. Org. Chem.*, 1995, 60, 6270; and Cohen et al., *Nucleic Acids Res.*, 1997, 25, 911), post-synthetic attachment of purified oligonucleotide conjugates to the support may still be advantageous for some applications. A variety of methods for tethering oligonucleotides to solid supports have been reported. Most of the methods are based on reactions of 5'-aminoalkyl conjugates of oligonucleotides with various functional groups on the support. For example, oligonucleotides bearing a 5'-terminal amino function have been attached to: (i) to carboxyalkylated polymer supports by carbodiimide assisted acylation (Ghosh and Musso, *Nucleic Acids Res.*, 1987, 15, 5353; Zhang et al., *Nucleic Acids Res.*, 1991, 19, 3929); (ii) amino-alkylated polymer supports by activation with 2,4,6-trichloro-1,3,5-triazine and subsequent displacement of one of the remaining chloro substituents with a resin bound amino group (Van Ness et al., *Nucleic Acids Res.*, 1991, 19, 3345); (iii) aldehyde-derivatized surfaces by reductive amination (Timofeev et al., *Nucleic Acids Res.*, 1996, 24, 3142); and (iv) phenyl-diisothiocyanate activated (Guo et al., *Nucleic Acids Res.*, 1994, 22, 5456) or epoxide-derivatized glass (Lamture et al., *Nucleic Acids Res.*, 1994, 22, 2121) surfaces by direct nucleophilic substitution. 5'-Phosphorylated oligonucleotides have been immobilized to aminoalkylated supports by carbodiimide-assisted phosphoramidate coupling (Ghosh and Musso, *Nucleic Acids Res.*, 1987, 15, 5353), and 5'-mercapto-functionalized oligonucleotides to mercaptoalkyl supports by disulfide formation (Bischoff et al., *Anal. Biochem.*, 1987, 164, 336). The latter oligonucleotides have also been successfully immobilized onto iodoacetamido-derivatized supports by nucleophilic α-substitution (O'Donnell et al., *Anal. Chem.*, 1997, 69, 2438).

Oligonucleotides bearing a 5'-terminal aldehyde function have been attached to aminoalkylated supports by reductive amination (Timofeev et al., *Nucleic Acids Res.*, 1996, 24, 3142), and to latex microspheres bearing hydrazine residues (Kremsky et al., *Nucleic Acids Res.*, 1987, 15, 2891). 2,4,6-Trichloro-1,3,5-triazine activation and disulfide bond formation have also been exploited in immobilization of 3'-amino and 3'-mercapto functionalized oligonucleotides, respectively (Hakala et al., *Bioconjugate Chem.*, 1997, 8, 232). Homopolymer-tailed oligomers have been attached to a nylon membrane by UV irradiation (Saiki et al., *Proc. Natl. Acad. Sci. U.S.A.*, 1989, 86, 6230).

The use of nucleic acid derived probes as diagnostic tools has seen widespread application. Typically, these probes are short oligonucleotides designed to bind to complementary target nucleic acids and have found applications in the detection of bacterial, viral and fungal infections, PCR reaction product, the study of polymorphisms, expression levels and genetic diseases. Their promise lies in the exquisite specificity and sensitivity of the hybridization reaction wherein the alteration or deletion of even one base leads to a dramatic change in the binding of the probe and target. Detection of the hybridized probe-target complex therefore allows for the identification of the nature and sequence of the target nucleic acid.

Diagnostic hybridization probes have been used in the art in homogenous conditions, such as in solution, and in heterogenous conditions, such as in mixed-phase hybridization assays. Mixed-phase hybridization assays typically utilize either the target or, more commonly, the probe in an immobilized form. Immobilization and mixed-phase hybridization have the primary advantage of ease of separation of the hybridized complex from excess reagents.

To further improve the utility of such diagnostic assays, arrays of nucleic acids have also been used. Such arrays of nucleic acid probes have provided advantages of parallel screening of nucleic acid targets, miniaturization, multiplexing and automation of such diagnostic procedures. Detection methods that have been commonly used in oligonulceotide probe diagnostic assays include radioactivity, fluorescent reporters, optical wave guides and mass spectrometry.

Such arrays have been used to sequence large nucleic acids via sequencing by hybridization (SBH). Typically, the probes are immobilized or a set of unknown targets are immobilized and sequentially hybridized with either the target nucleic acids or oligonucleotide probes, respectively. Tiling arrays have been widely used to systematically identify the base at each position of an unknown nucleic acid (Chee et al., Science, 274 (1996) 610–614). Tiling arrays have been used in polymorphism studies of the HIV Protease gene (Kozal et al., Nat. Med., 2 (1996) 753–9), and for mutation studies of hereditary breast cancer gene BRCA1 (Hacia et al., Nucleic Acids Res., 26 (1998) 3865–66) and cystic fibrosis (Cronin et al., Human Mut., 7 (1996) 244–55). Oligonucleotide arrays have also been used in combination with enzymes such as ligases and polymerases to provided enhanced methods of mutation analysis.

It has been recognized that oligonucleotides having reactive groups capable of reacting with specific reporter groups, ligands, cell surface targeting agents, mRNA target cleavage agents, solid supports, nylon membranes, silicon chips, glass plates, glass slides and microparticles are of great importance in the development of oligonucleotides that are useful as research reagents, diagnostic agents and therapeutic agents, as well as in DNA arrays.

SUMMARY OF THE INVENTION

In accordance with the present invention, oligomers containing aminooxy linkages are provided. Preferred compositions include oligomers comprising a plurality of nucleotide units of the structure:

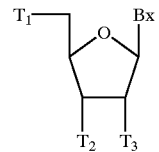

wherein:

Bx is a purine or pyrimidine heterocyclic base;

each $T_1$ and $T_2$ is, individually, OH, a protected hydroxyl, a nucleotide, a nucleoside or an oligonucleotide;

$T_3$ is H, OH, a protected hydroxyl or a sugar substituent group;

said oligomer further comprising at least one group, R, therein; said R group occurring at the 5'-end, the 3'-end, in lieu of at least one $T_3$ or as a substituent on at least one Bx; said R group having one of the formulas:

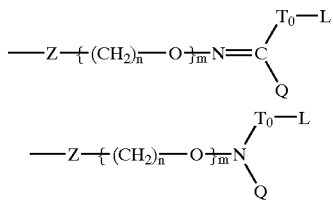

wherein:
each Z is, independently, a single bond, O or a phosphate;
each Q is, independently, H, $C_1$–$C_{10}$ alkyl or a nitrogen protecting group;
each $T_0$ is, independently, a bond or a linking moiety;
each L is, independently, a chemical functional group, a conjugate group or a solid support material;
or Q, $T_0$ and L, together, are a chemical functional group;
each m is, independently, an integer from 1 to about 10; and
each n is, independently, an integer from 1 to about 6.

In a preferred embodiment, R is a conjugate group. In another preferred embodiment, R is a solid support material. In yet another embodiment, R is a chemical functional group.

In a preferred group of compounds the conjugate group is a contrast reagent, a cleaving agent, a cell targeting agent, polyethylene glycol, cholesterol, phospholipid, biotin, phenanthroline, phenazine, phenanthridine, anthraquinone, acridine, fluorescein, rhodamine, coumarin, pyrene, retinal or a cyanine dye. In another preferred group of compounds the solid support material is microparticles or CPG.

The present invention also provides methods for diagnosing the presence of nucleic acids in a sample comprising the steps of attaching an oligonucleotide containing an aminooxy linkage to a solid support material; labeling the oligonucleotide with a marker to form a labeled oligonucleotide; treating the labeled oligonucleotide with a target oligonucleotide to form a hybridization mixture; detecting binding of the labeled oligonucleotide with the target oligonucleotide in the hybridization mixture; and determining the amount of labeled oligonucleotide bound to the target oligonucleotide.

The present invention also provides another method of diagnosing the presence of nucleic acids in a sample comprising the steps of attaching an oligonucleotide containing an aminooxy linkage to a solid support material; treating the oligonucleotide with a target oligonucleotide to form a hybridization mixture, wherein the target oligonucleotide is labeled with a marker; detecting binding of the oligonucleotide with the target oligonucleotide in the hybridization mixture; and determining the amount of oligonucleotide bound to the target oligonucleotide.

In a preferred embodiment the solid support material comprises an aldehyde group. In another preferred embodiment the solid support material comprises an epoxy group. In yet another preferred embodiment the solid support material is microparticles. It is preferred that the marker be a fluorescent marker. It is also preferred that the labeling step comprise forming a lanthanide chelate with the oligonucleotide. It is further preferred that the detecting step comprise measuring the fluorescence emission of the hybridization mixture.

DETAILED DESCRIPTION OF PREFERRED EMBODIMENTS

Figure 1:
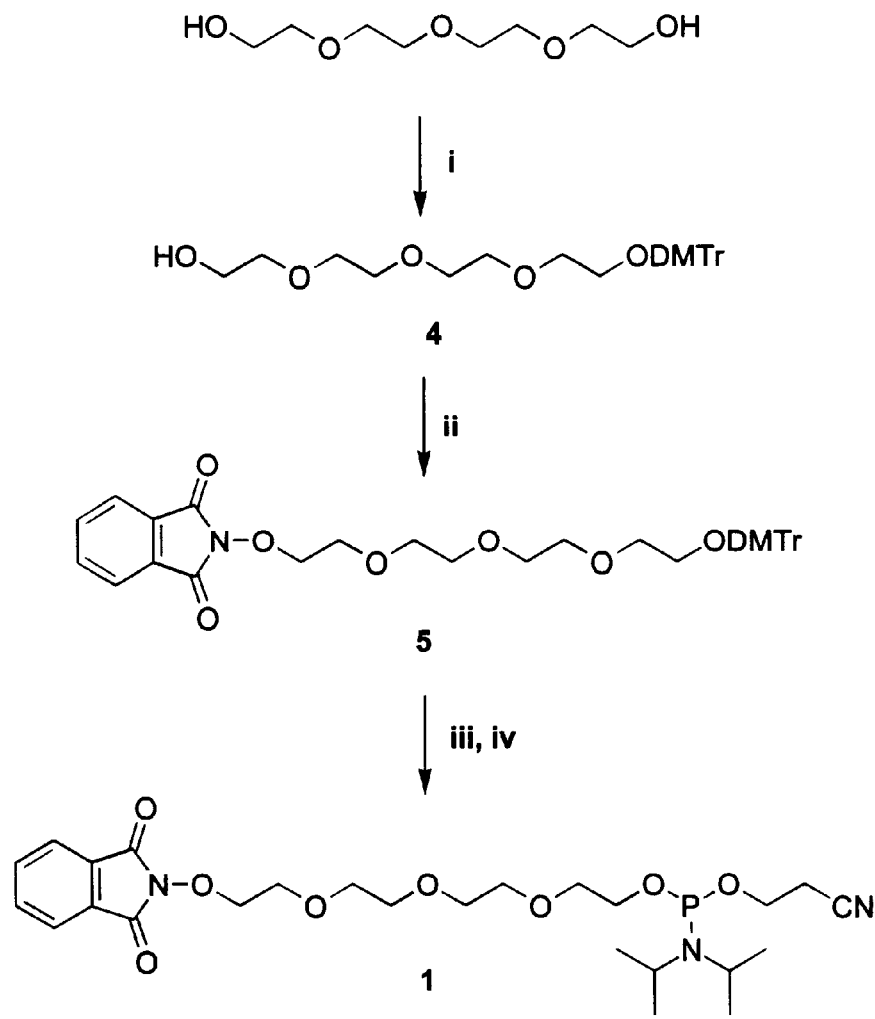
FIG. 1 is a schematic showing the synthesis of compound 1.
Figure 2:
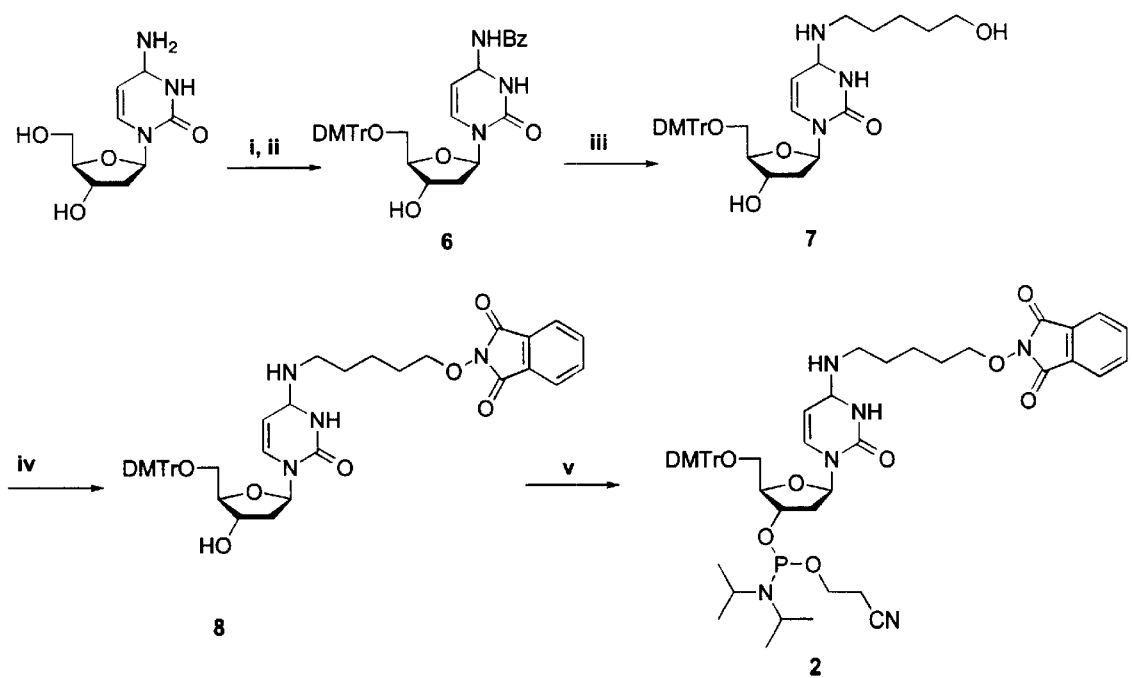
FIG. 2 is a schematic showing the synthesis of compound 2.
Figure 3:
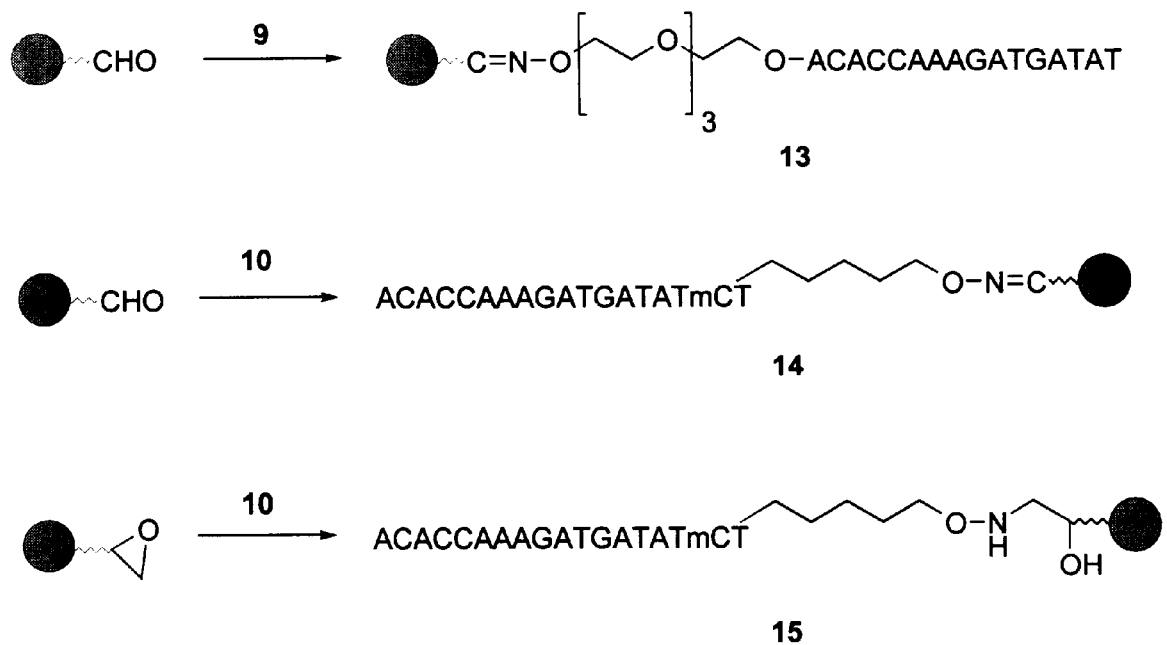
FIG. 3 is a schematic showing the attachment of oligonucleotides 9 (SEQ ID NO:1) and 10 (SEQ ID NO:2) to microparticles, forming particle-bound conjugates 13, 14 and 15.
Figure 4:
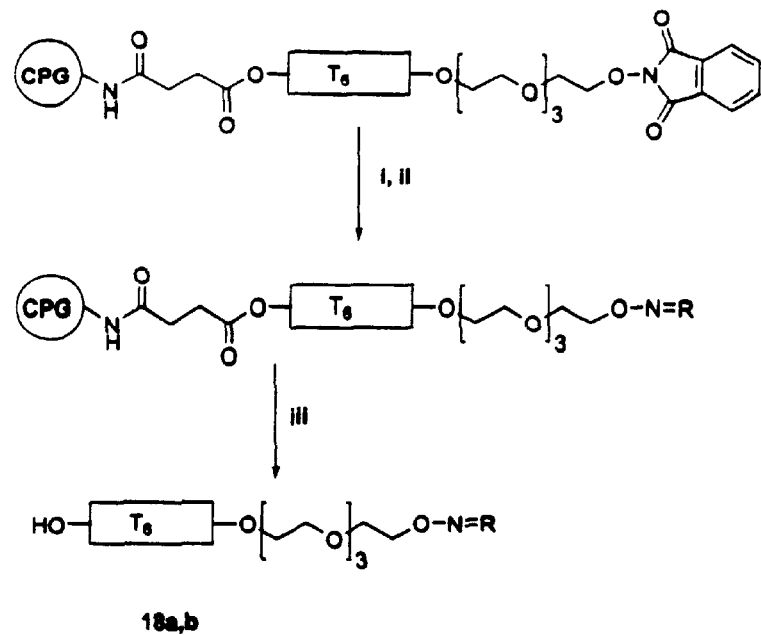
FIG. 4 is a schematic showing the synthesis of compounds 18a, 18b, 19a and 19b.
Figure 4:
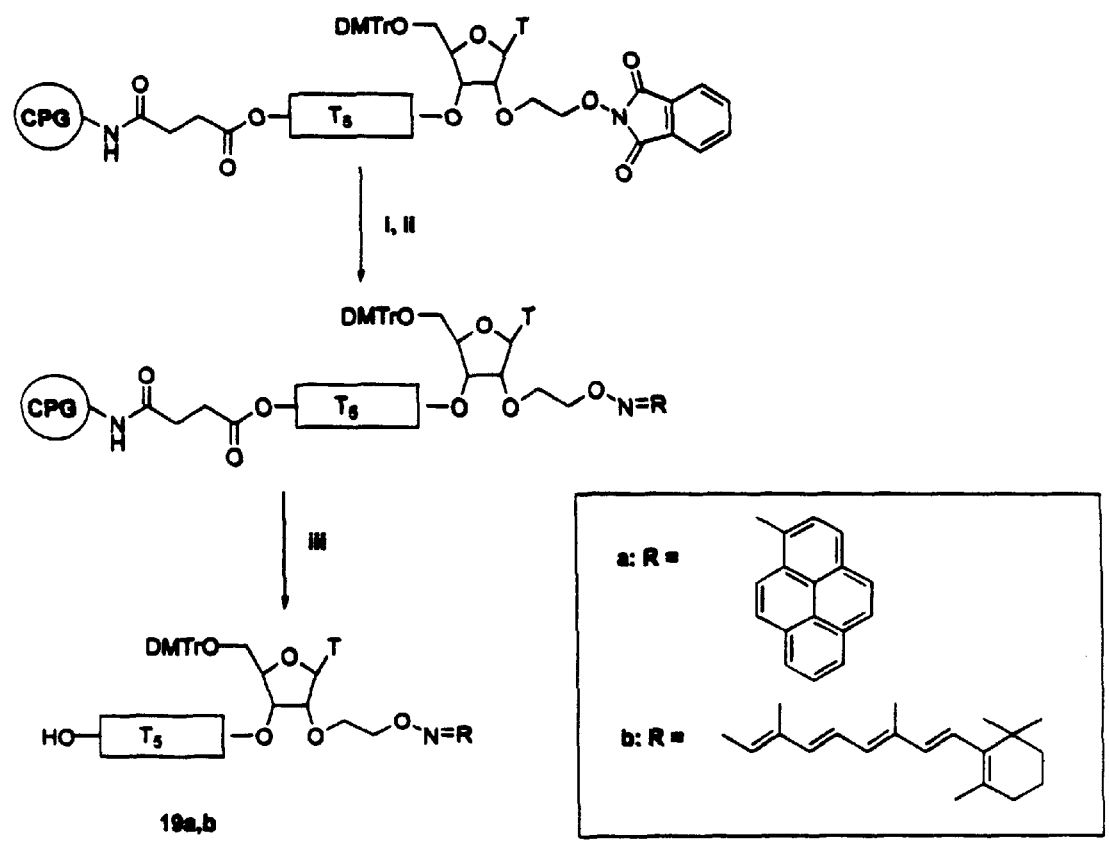
Figure 5:
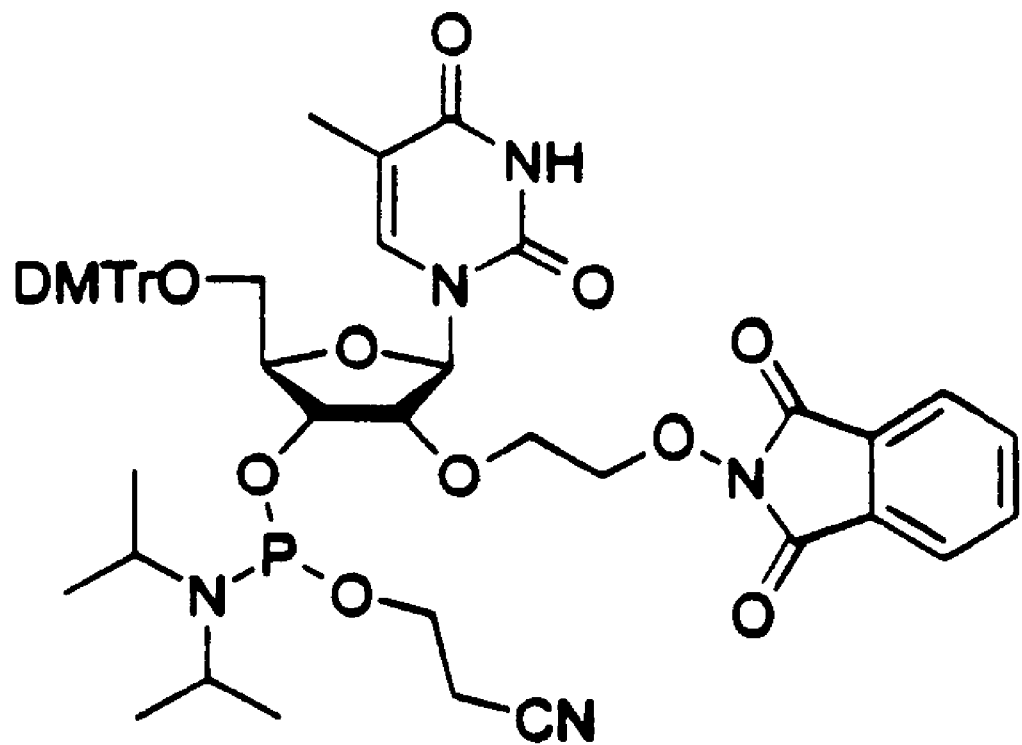
FIG. 5 shows the structure of phosphoramidite 5.
Figure 6:
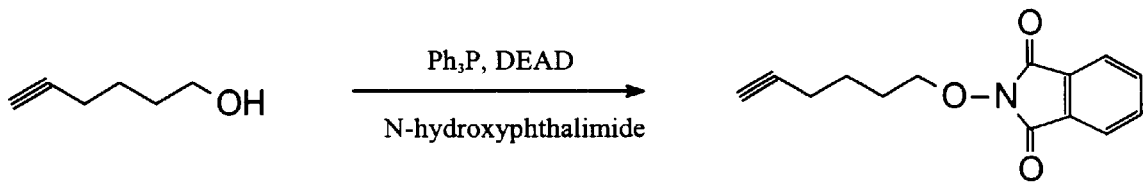
FIG. 6 is a schematic showing the synthesis of 1-phthalimidooxy-hex-5-yne.
Figure 7:
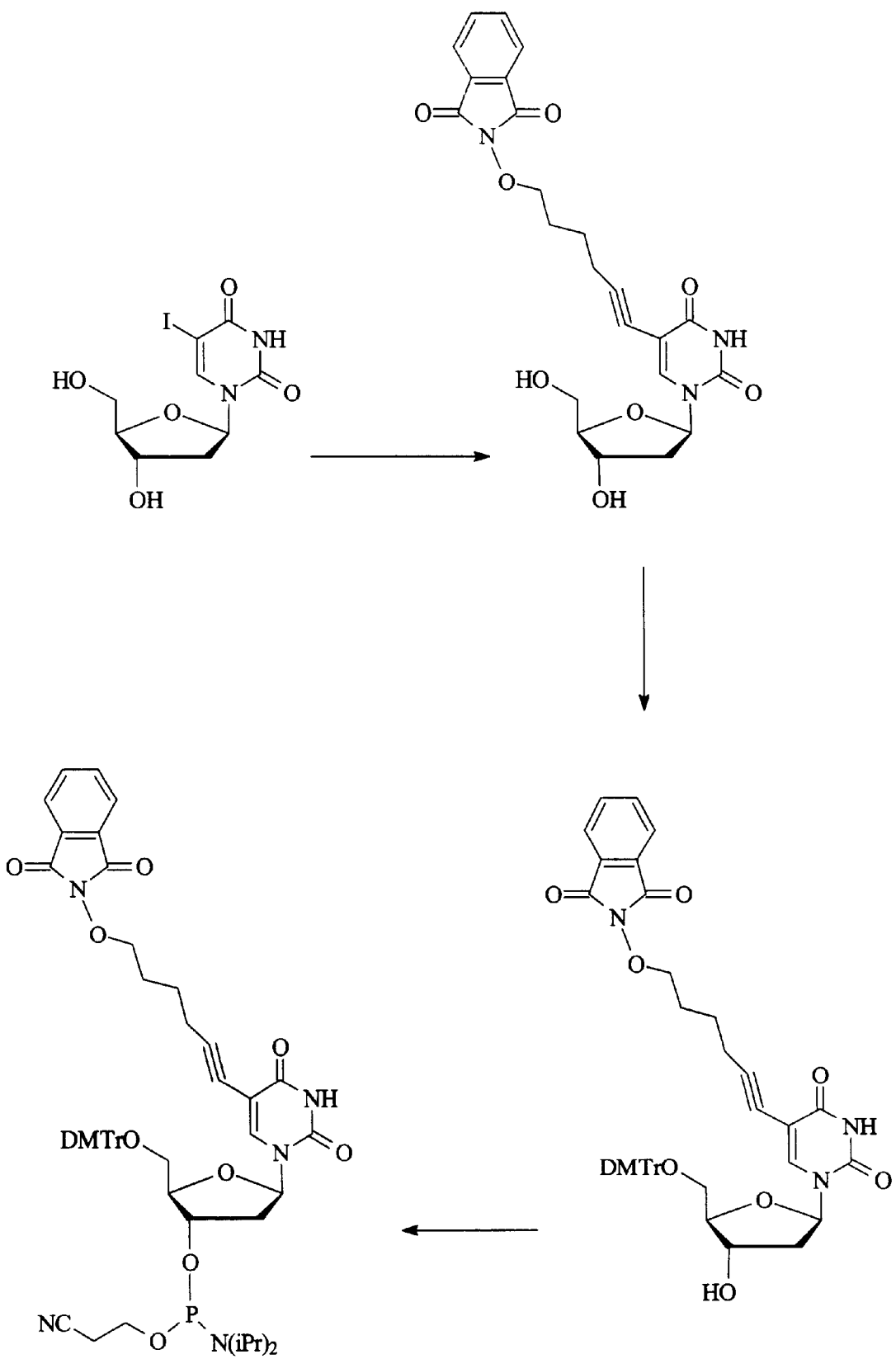
FIG. 7 is a schematic showing the synthesis of 5'-O-DMT-5-(6-phthalimidooxyhex-1-ynyl)-uridine-3'-O-[(2-cyanoethyl)N,N-diisopropyl]phosphoramidite.
Figure 8:
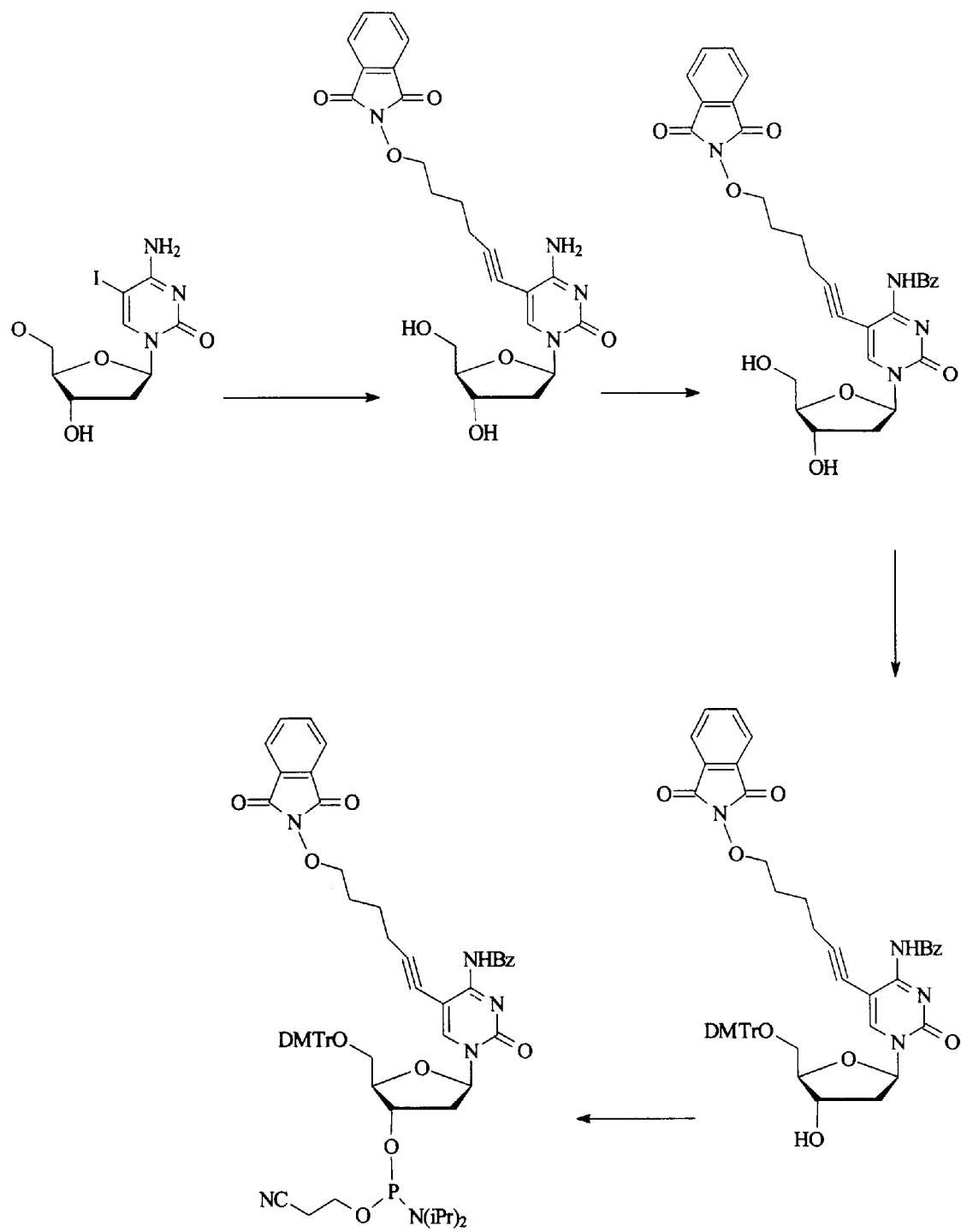
FIG. 8 is a schematic showing the synthesis of 5'-O-DMT-$N^4$-benzoyl-5-(6-phthalimidooxyhex-1-ynyl)-2'-deoxy-cytidine-3'-O-[(2-cyanoethyl)N,N-diisopropyl] phosphoramidite.
Figure 9:
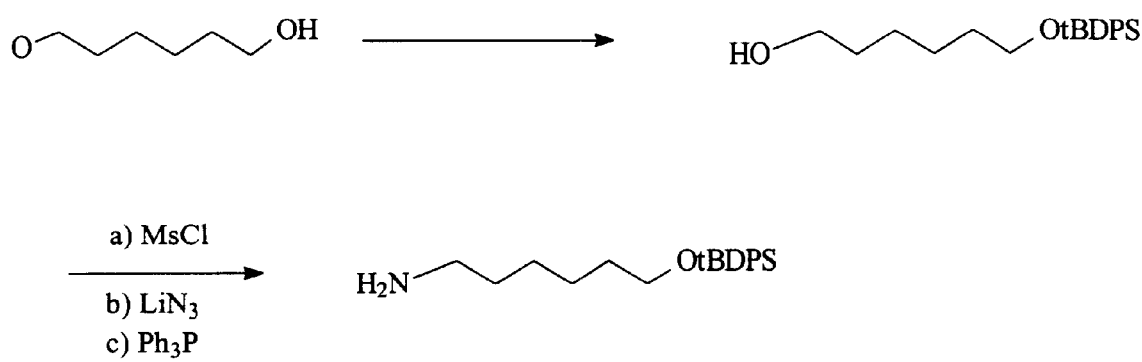
FIG. 9 is a schematic showing the synthesis of 1-t-butyldiphenylsilyl-6-aminohexanol.
Figure 10:
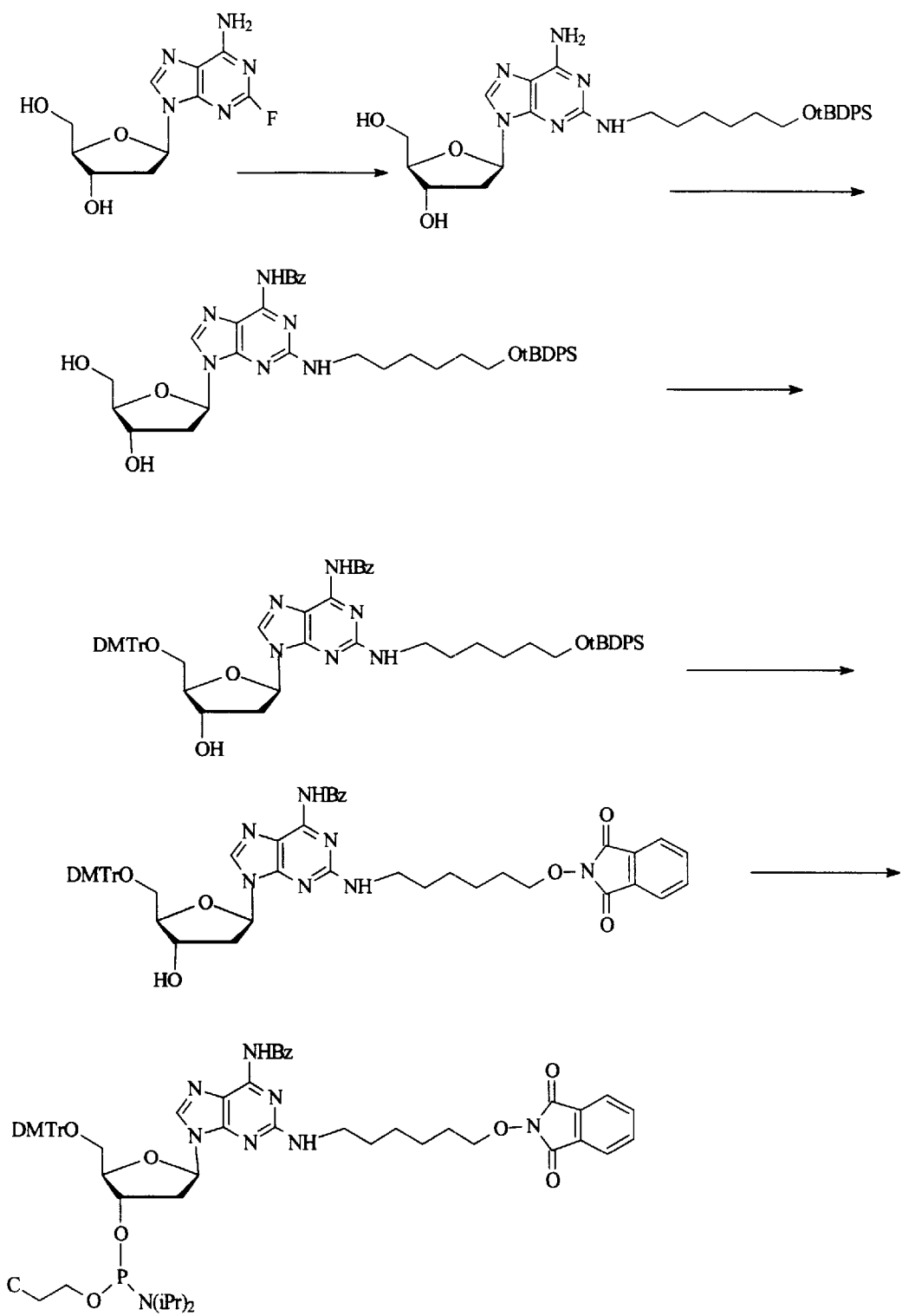
FIG. 10 is a schematic showing the synthesis of 5'-O-DMT-2-(6-phthalimidooxy-aminohexyl)-2'-deoxyadenosine-3'-O-[(2-cyanoethyl)N,N-diisopropyl] phosphoramidite.
Figure 11:
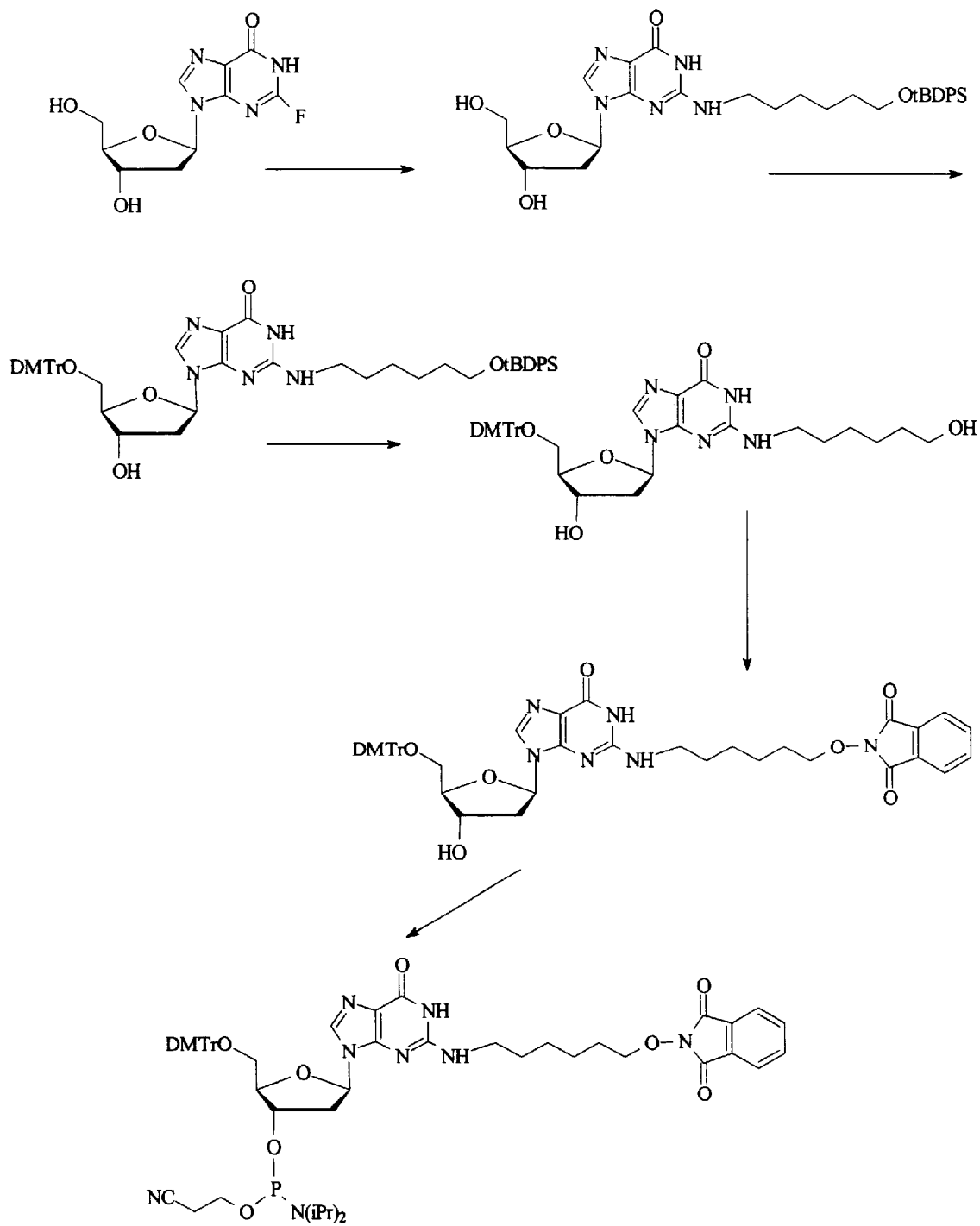
FIG. 11 is a schematic showing the synthesis of 5'-O-DMT-2-(6-phthalimidooxy-aminohexyl)-2'-deoxyinosine-3'-O-[(2-cyanoethyl)N,N-diisopropyl]phosphoramidite.
Figure 12:
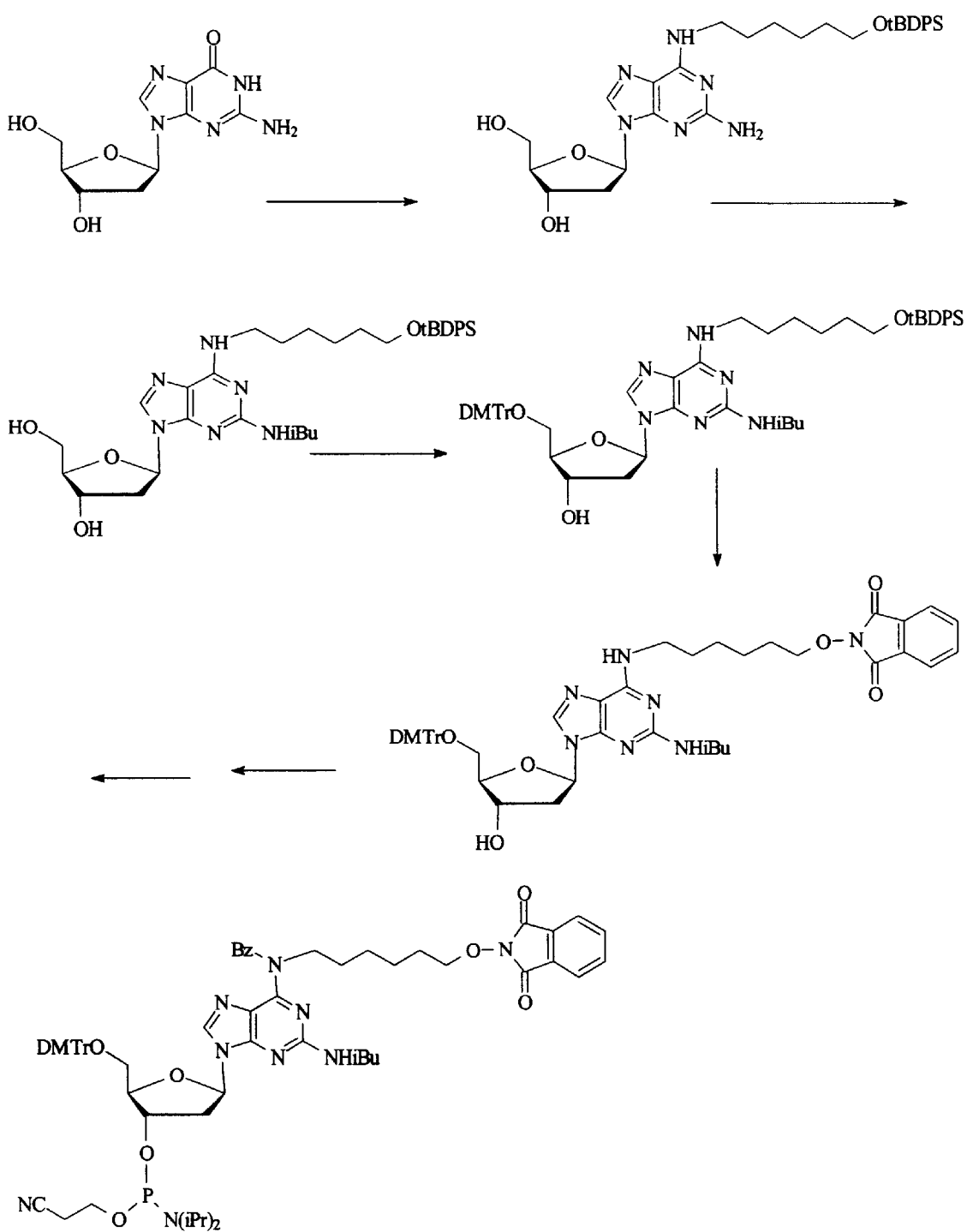
FIG. 12 is a schematic showing the synthesis of 5'-O-DMT-N2-isobutyryl-N6-(6-phthalimidooxy-hexyl)-2'-deoxy-adenosine-3'-O-[(2-cyanoethyl)N,N-diisopropyl]-phosphoramidite.

The present invention provides oligomers containing aminooxy functionalities. These aminooxy groups serve as tethers or form linkages with solid support materials. The aminooxy functionality is masked with a protecting group such a phthalimido moiety. The phosphoramidites of the present invention bearing a masked aminooxy group are incorporated into oligonucleotides. These aminooxy building blocks enable tethering of the aminooxy group either at 5'-terminus or the 3'-terminus of the oligonucleotide, or at the 2'-position of the sugar moiety. This aminooxy group or functionality may also be attached to the heterocyclic base at any desired position within the oligonucleotide sequence. The protected aminooxy functionality may be introduced into the phosphoramidite building blocks by displacing a hydroxy group with N-hydroxyphthalimide under the well-known Mitsunobu reaction conditions (Synthesis, 1981, 1). The phthaloyl protection was removed from the aminooxy functionality of the assembled oligonucleotide conjugates with hydrazinium acetate. The normal succinyl linker withstands this treatment, and hence the support-bound oligonucleotides may be converted, when desired, to more stable oxime conjugates prior to conventional ammonolytical base moiety deprotection and release from the support. The deprotected aminooxy tethered oligonucleotides may further be immobilized to polymer microparticles or another solid support bearing either aldehyde or epoxide functionalities. Alternatively, aminooxy tethered oligonucleotides may be attached to aldehyde or epoxide containing linkers, which in turn may be attached to polymer microparticles or another solid support. In mixed-phase hybridization assays, oligonucleotide-coated particles function in the same manner as oligonucleotides prepared by methods established previously for post-synthetic immobilization.

The present invention further provides improved methods for the detection of nucleic acids and validation of nucleic acid targets. The present invention provides methods for the application of microparticles to the detection of nucleic acids by sequencing by hybridization (SBH). The methods of the present invention accomplish this by using time resolved fluorescence in the presence of a lanthanide chelate as the method of detecting the hybridization between individual microparticle probes and target nucleic acids. Further, these microparticle methods may be extended to multiparametric assays that are capable of rapid, parallel screening and analysis of unknown nucleic acids and target validation. Lanthanide chelates used in the methods of the present invention include, but are not limited to, lanthanide ions such as Eu+3, Tb+3, Sm+3 and Dy+3, and organic ligands such as 2,2', 2",2"'-{{4'-{4'''-[(4,6-dichloro-1,3,5-tirazin-2-yl)amino]phenyl}-2,2':6',2"-terpyridine-6,6"-diyl}bis-(methylenenitrilo)}-tetrakisacetate.

Oligonucleotides may be covalently attached to microparticles either in a post-synthetic manner or via in situ synthesis of the oligonucleotide on the particle. The post-synthetic approach is more laborious but the immobilized oligonucleotide is pure and hence homogenous coating of the microparticle is achieved. In contrast, the more convenient in situ synthesis generates heterogenous probes depending on the coupling efficiency during synthesis.

Post-synthetic immobilization of oligonucleotide probes may be accomplished on a wide variety of microparticles such as those made from, but not limited to, controlled pore glass, nylon, latex, Sephacryl polyacrylamide, and magnetic materials. See, Tang et al., Nucleic Acids Res., 23 (1995) 3126–31; Van Ness et al., Nucleic Acids Res., 19 (1991) 3345–50; Kremsky et al., Nucleic Acids Res., 15 (1987) 2891–2909; Kwoh et al., Proc. Natl. Acad. Sciences USA, 86 (1989) 1173–77; Fahy et al., Nucleic Acids Res., 21 (1993) 1819–26). Particle size can vary from sub-micron particles (diameter<1 micron) to those that may be several hundred microns in size. With sub-micron particles hybridization may be accomplished at rates similar to those seen in solution while larger particles afford higher levels of loading of the oligonucleotide.

Immobilization of oligonucleotides onto microparticles may be accomplished via derivatization of the amino groups pendant from the microparticle. The amino groups are first subjected to an acylation reaction using either dithioglycolic acid, 10-undecenoic acid or N-Fmoc-β-alanine followed by capping of unreacted amino groups of the support. The dithioglycolate is reduced to afford a thiol derivatized microparticle. The undecenoate is subjected to radical addition of thioacetic acid across the double bond followed by ammonolysis to afford a thiol group attached to the microparticle. The Fmoc-β-alanine derivatized microparticles are treated with a solution of morpholine in pyridine to cleave the Fmoc group and afford a pendant amino group on the microparticle.

Probe oligonucleotides were prepared as 3'-modified oligonucleotides using a non-nucleosidic solid support developed by Hovinen et al. (Tetrahedron, 50 (1994) 7203–18) followed by release of the oligonucleotide from the support using either cystamine or ethylenediamine. The resulting 3'-protected mercapto or free amino bearing oligonucleotides were subsequently activated and then reacted with the mercapto or amino microparticles. Alternatively, 3'-amino oligonucleotides may be activated using 2,4,6-trichloro-triazine prior to reaction with amino derivatized microparticles. The oligonucleotide loading of the particles ranged from 0.7 to 8 micromoles/g.

Instead of post-synthetic attachement of oligonucleotides to the microparticles, in situ synthesis of the oligonucleotides may be used to prepare the desired immobilized oligonucleotide probes. Typically, porous amino derivatized microparticles are used directly in automated oligonucleotide synthesis to afford the desired oligonucleotide derivatized microparticles. Microparticles prepared by in situ synthesis were observed to have hybridization properties similar to those prepared via post-synthetic attachment.

Categorization of particles refers to incorporation of labels, and may be accomplished either during preparation of the particles by polymerization or subsequently (post-synthesis) by the user. These labels are also referred to as tags or markers. Labels which are of use according to the methods of the present invention include radiolabels as well as labels that can be detected by ELISA and other immunoassays. Radiolabels may be detected by measuring the radioactivity of the molecule containing the radiolabel. Labels that are of use in an immunoassay can be detected by a sandwich hybridization assay such as an ELISA assay. Biotin is a preferred label.

Fluorescent labels or markers are also preferred and may be conveniently introduced into the oligonucleotide via the use of fluorescent phosphoramidites during automated oligonucleotide synthesis. Any of a wide variety of commercially available fluorescent markers and dyes may be used; preferably 1-(4,4'-dimethoxy-trityloxy)-2-[N-thiourea-(di-O-pivaloylfluorescein)-4-aminobutyl]propyl-3-O-(2-cyanoethyl)-(N,N-iisopropyl)-phsophoramidite and N4-(N-dansyl-6-aminohexyl)-2'-deoxy-5'-O-(4,4'-dimethoxy-trityl)cytidine are employed in the methods of the present invention. Labels may be incorporated anywhere in the oligonucleotide, however attachment towards the center of the probe nucleic acid is preferred. Through the appropriate mixing of different fluorescent labels on the same oligonucleotide a large array of uniquely labeled microparticles may be prepared.

Any of the generally known heterogenous hybridization assays may be rapidly applied to the derivatized microparticles and methods of the present invention. Two of the preferred hybridization methods of the invention include the use of a fluorescently-labeled target oligonucleotide, as may be done for PCR products, and the sandwich type assay. See, Hakala and Lonnberg, Bioconjugate Chem., 8 (1997) 232–37; Hakala et al., Bioconjugate Chem., 8(1997) 378–384; Hakala et al., Bioconjugate Chem., 9 (1998) 316–21. Accordingly, an oligonucleotide bearing a fluroescent tag may be hybridized to the complementary 3'-terminal sequence of a target oligonucleotide and the resulting duplex further hybridized to the particle bound probe via the 5'-terminal sequence of the target. Fluorescence emission may be measured directly on a single particle using a microfluorometer, and the number of fluorescently labeled oligonucleotides hybridized to the particle may be calculated. See, Hakala and Lonnberg, Bioconjugate Chem., 8 (1997) 232–37; Hakala et al., Bioconjugate Chem., 8 (1997) 378–384; Hakala et al., Bioconjugate Chem., 9 (1998)

316–21). In this manner, the microparticles of the present invention may be used in diagnostic assays.

The hybridization kinetics of the microparticles of the present invention depend on the structure of the linker employed to tether the oligonucleotide to the particle. Surprisingly, the density of the immobilized oligonucleotides on the particle has no effect on the hybridization kinetics. Further, concentration of the flourescent oligonucleotide does not affect kinetics, but the density of the microparticles in solution does. Hybridization efficiency of the particles was found to be independent of the concentration of the labeled complementary or target nucleic acid over a wide range. Efficiency was also independent of the density of oligonucleotide covalently immobilized to the particles. The kinetics of the sandwich type hybridization are very similar to those observed for direct hybridization. Efficiency of sandwich hybridizations increased with increasing concentration of the target.

Multiparametric assays, that is detection of several oligonucleotides in parallel, may be carried out using a mixture of the categorized microparticles. This type of assay is particularly desirable when studying disease-related mutations having high degrees of allelic diversity. By using multiple fluorescent labels and mixing them in different proportions, the microparticle arrays of the present invention may be tailored to assay a wide range of test nucleic acids. The advantages of this multiparametric method is that each particle category works independently in the assay mixture; neither the presence of particles belonging to another category nor the presence of additional targets has any effect on the efficiency and kinetics of hybridization. This method may be applied successfully to identify, for example, a three base deletion, point mutation and a point deletion related to cystic fibrosis.

By using a mixture of categorized microparticles that employ time resolved fluorescence for detection of hybridization events, the methods of the present invention provide a means for the rapid, parallel analysis of unknown nucleic acids, their sequencing and target validation. The methods of the present invention offer the advantages of an exceptionally large dynamic range of 5 orders of magnitude and exceptionally low sensitivity limits that are in the sub-attamole range for a single particle.

As used herein, "aminooxy linkage," aminooxy tether" or "aminooxy functionality" denotes a hydrocarbyl group having an oxygen atom linked to a nitrogen atom or an amino moiety.

Heterocyclic bases amenable to the present invention include both naturally- and non-naturally-occurring nucleobases and heterocycles. A representative list includes adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 7-methylguanine, 5-trifluoromethyl and other 5-substituted uracils and cytosines. Further heterocyclic bases include those disclosed in U.S. Pat. No. 3,687,808; the *Concise Encyclopedia Of Polymer Science And Engineering,* pages 858–859, Kroschwitz, J. I., Ed., John Wiley & Sons, 1990; and Englisch et al., *Angewandte Chemie,* International Edition, 1991, 30, 613.

Heterocyclic bases in the oligomers of the present invention may be covalently bound to an R group. In a preferred embodiment, the R group may be covalently attached to C4 or C5 of a pyrimidine heterocyclic base. In another preferred embodiment, the R group may be covalently attached to N2 or N6 of a purine heterocyclic base.

Conjugate groups of the invention include intercalators, reporter molecules, contrast reagents, cleaving agents, cell targeting agents, cyanine dyes, polyamines, polyamides, poly ethers including polyethylene glycols, and other moieties known in the art for enhancing the pharmacodynamic properties or the pharmacokinetic properties. Typical conjugate groups include PEG groups, cholesterols, phospholipids, biotin, phenanthroline, phenazine, phenanthridine, anthraquinone, acridine, fluoresceins, rhodamines, coumarins, pyrene, retinal and dyes.

The methods according to the present invention are performed in various traditional solvents either utilizing solution phase techniques or automated synthetic protocols. Many solvents for automated oligonucleotide synthesis as well as solution phase oligonucleotide synthesis are known in the art. Preferred solvents include DMF, DMSO, THF, THP and $CH_3CN$.

Standard solution phase and solid phase methods for the synthesis of oligonucleotides and oligonucleotide analogs are well known to those skilled in the art. These methods are constantly being improved in ways that reduce the time and cost required to synthesize these complicated compounds. Representative solution phase techniques are described in U.S. Pat. No. 5,210,264, issued May 11, 1993 and commonly assigned with this invention. Representative solid phase techniques employed for oligonucleotide and oligonucleotide analog synthesis utilizing standard phosphoramidite chemistries are described in "Protocols For Oligonucleotides And Analogs," Agrawal, S., Ed., Humana Press, Totowa, N.J., 1993.

A representative list of chemical functional groups according to the invention include $C_1$–$C_{10}$ alkyl, substituted $C_1$–$C_{10}$ alkyl, $C_2$–$C_{25}$ alkenyl, substituted $C_2$–$C_{25}$ alkenyl, $C_2$–$C_{15}$ alkynyl, substituted $C_2$–$C_{15}$ alkynyl, $C_4$–$C_7$ carbocyclic alkyl, substituted carbocyclic alkyl, alkenyl carbocyclic, substituted alkenyl carbocyclic, alkynyl carbocyclic, substituted alkynyl carbocyclic, $C_6$–$C_{20}$ aryl, substituted $C_6$–$C_{20}$ aryl, heteroaryl, substituted heteroaryl, a nitrogen, oxygen, or sulfur containing heterocycle, a substituted nitrogen, oxygen, or sulfur containing heterocycle, a mixed heterocycle, or a substituted mixed heterocycle, where said substituent groups are selected from alkyl, alkenyl, alkynyl, aryl, hydroxyl, alkoxy, alcohol, benzyl, nitro, thiol, thioalkyl, thioalkoxy, or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine ($C((=NH)NR^2R^3)$), guanidine ($NHC(=NH)NR^2R^3$), glutamyl ($R^1OOCCH(NR^2R^3)(CH_2)_2C(=O)$), nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding, wherein each $R^1$ and $R^2$ is, independently, H, haloalkyl, $C_1$–$C_{10}$ alkyl, $C_2$–$C_{10}$ alkenyl, $C_2$–$C_{10}$ alkynyl, or $C_6$–$C_{14}$ aryl; and each $R^3$ is, independently, a single bond, CH=CH, C≡C, O, S, $NR^6$, $SO_2$, $C_6$–$C_{14}$ aryl, substituted $C_6$–$C_{14}$ aryl, heteroaryl, substituted heteroaryl, a nitrogen, oxygen, or sulfur containing heterocycle, a substituted nitrogen, oxygen, or sulfur containing heterocycle, a mixed heterocycle, or a substituted mixed heterocycle, wherein said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups.

In a preferred embodiment, the chemical functional group is a pyrenyl group. In another preferred embodiment, the chemical functional group is a retinolyl group.

A number of chemical functional groups can be introduced into compounds of the present invention in a blocked form and can then be subsequently deblocked to form the final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido, 9-fluorenylmethoxycarbonyl (FMOC), triphenylmethylsulfenyl, t-BOC or benzyl groups. Carboxyl groups can be protected as acetyl groups. Representative hydroxyl protecting groups are described by Beaucage et al. (Tetrahedron 1992, 48, 2223). Preferred hydroxyl protecting groups are acid-labile, such as trityl, monomethoxytrityl, dimethoxytrityl, trimethoxytrityl, 9-phenylxanthine-9-yl (Pixyl) and 9-(p-methoxyphenyl)-xanthine-9-yl (MOX). Chemical functional groups can also be "blocked" by including them in a precursor form. Thus an azido group can be considered to be a "blocked" form of an amine as the azido group may be easily converted to the amine. Further representative protecting groups utilized in oligonucleotide synthesis are discussed in Agrawal et al., Protocols for Oligonucleotide Conjugates, Humana Press, N.J., 1994, Vol. 26, pp. 1–72.

In the context of the present invention, a "heterocycle" is a cyclic compound containing at least one heteroatom such as N, O or S. A "mixed heterocycle" is a cyclic compound containing at least two heteroatoms such as N, O or S. A "heteroaryl" compound is a heterocycle containing at least one heteroatom such as N, O or S and is not fully saturated, e.g., is in a state of partial or complete saturation. "Heteroaryl" is also meant to include fused systems including systems where one or more of the fused rings contain no heteroatoms. "Heterocycles," including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

As used herein, "linking moiety" refers to O, NH, S, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are selected from hydroxyl, alkoxy, alcohol, benzyl, phenyl, nitro, thiol, thioalkoxy, halogen, alkyl, aryl, alkenyl and alkynyl.

"Conjugate groups" according to the present invention include those known in the art. A representative list of conjugate groups amenable to the present invention includes intercalators, reporter molecules, contrast reagents, cleaving agents, cell targeting agents, cyanine dyes, polyamines, polyamides, poly ethers including polyethylene glycols, and other moieties known in the art for enhancing the pharmacodynamic properties or the pharmacokinetic properties. Typical conjugate groups include PEG groups, cholesterols, phospholipids, biotin, phenanthroline, phenazine, pyrene, retinal, phenanthridine, anthraquinone, acridine, fluoresceins, rhodamines, coumarins, and dyes.

Oligomeric compounds are synthesized having one or more chemically bound fluorescent labels (a fluorophore) to facilitate detection by LIF. A representative list of fluorophores includes fluorescein, dansyl, fluorescamine, OPA, NDA, ethidium bromide, acridine, JOE, FAM and rhodamine. Other fluorohores precursors are sold by Molecular Probes, Inc. Eugene, Oreg. A useful group of these are listed in PCT publication WO 92/03464. Thus as will be apparent to those of skill in the art, there exists a wide variety of commercially available fluorophores which are suitable for use in the present invention. Chemical bonding of fluorescent labels, with or without a linking or tethering group, to oligomeric compounds is well known in the art. Typically, the fluorescent label is attached via a covalent bond using a tethering moiety.

As used herein the term "sugar substituent group" or "2'-substituent group" includes groups attached to the 2' position of the ribosyl moiety with or without an oxygen atom. 2'-Sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl),m, where m is 1 to about 10. Preferred among these polyethers are linear and cyclic polyethylene glycols (PEGs), and PEG-containing groups, such as crown ethers, and other reported substituent groups. See, Ouchi et al., Drug Design and Discovery 1992, 9, 93; Ravasio et al., J. Org. Chem. 1991, 56, 4329; and Delgardo et. al., Critical Reviews in Therapeutic Drug Carrier Systems 1992, 9, 249. Each of the foregoing references is hereby incorporated by reference in its entirety. Further sugar substituent groups are disclosed by Cook (Anti-Cancer Drug Design, 1991, 6, 585–607). Fluoro, O-alkyl, O-alkylamino, O-alkyl imidazole, O-alkylaminoalkyl, and alkyl amino substituents are described in U.S. patent Ser. No. 6,166,197, filed Mar. 6, 1995, entitled "Oligomeric Compounds having Pyrimidine Nucleotide(s) with 2' and 5' Substitutions," hereby incorporated by reference in its entirety.

Additional 2' sugar modifications amenable to the present invention include 2'-SR and 2'-$NR_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., J. Org. Chem., 1997, 62, 3415–3420. 2'-$NR_2$ nucleosides are disclosed by Goettingen, M., J. Org. Chem., 1996, 61, 6273–6281; and Polushin et al., Tetrahedron Lett., 1996, 37, 3227–3230. Further representative 2'-O-sugar modifications amenable to the present invention include those having one of formula I or II:

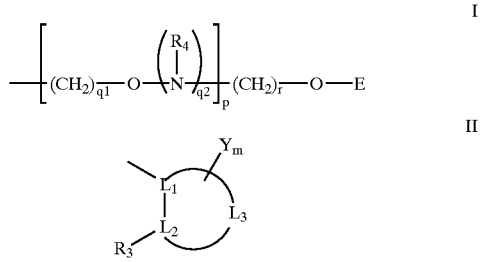

wherein:

E is $C_1$–$C_{10}$ alkyl, $N(R_4)(R_5)$ or $N=C(R_4)(R_5)$ each $R_4$ and $R_5$ is, independently, H, $C_1$–$C_{10}$ alkyl, a nitrogen protecting group, or $R_4$ and $R_5$, together, are a nitrogen protecting group or are joined in a ring structure that includes at least one additional heteroatom selected from N and O;

$R_3$ is OX, SX, or $N(X)_2$;

each X is, independently, H, $C_1$–$C_8$ alkyl, $C_1$–$C_8$ haloalkyl, C(=NH)N(H)Z, C(=O)N(H)Z or OC(=O)N(H)Z;

Z is H or $C_1$–$C_8$ alkyl;

$L_1$, $L_2$ and $L_3$ comprise a ring system having from about 4 to about 7 carbon atoms or having from about 3 to about 6 carbon atoms and 1 or 2 heteroatoms, said heteroatoms being selected from oxygen, nitrogen and sulfur, wherein said ring system is aliphatic, unsaturated aliphatic, aromatic, or saturated or unsaturated heterocyclic;

Y is $C_1$–$C_{10}$ alkyl or haloalkyl, $C_2$–$C_{10}$ alkenyl, $C_2$–$C_{10}$ alkynyl, $C_6$–$C_{14}$ aryl, $N(R_4)(R_5)$ $OR_4$, halo, $SR_4$ or CN;

each $q_1$ is, independently, an integer from 2 to 10;

each $q_2$ is 0 or 1;

p is an integer from 1 to 10; and r is an integer from 1 to 10;

provided that when p is 0, r is greater than 1.

Representative 2'-O-sugar substituents of formula I are disclosed in U.S. Pat. Ser. No. 6,172,209 filed Aug. 7, 1998, entitled "Capped 2'-Oxyethoxy Oligonucleotides," hereby incorporated by reference in its entirety.

Representative cyclic 2'-O-sugar substituents of formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Further, in the context of the present invention, aryl groups (generally $C_6$–$C_{20}$) include but are not limited to substituted and unsubstituted aromatic hydrocarbyl groups. Aralkyl groups (generally $C_7$–$C_{20}$) include, but are not limited to, groups having both aryl and alkyl functionalities, such as benzyl and xylyl groups. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, alkyl, aryl, alkenyl, or alkynyl groups.

As used herein, "arrays" are systematic collections of nucleic acids, preferably probes, that are organized in a known pattern, attached to a solid support such as a glass slide, silicon chip, polypropylene support, or polyacrylamide gel pads. Nucleic acid arrays are known in many different forms including two-dimensional and three-dimensional arrays, offset scanning arrays, and photolithographic arrays.

Further classification of arrays is possible based on the manner in which the array is fabricated: via in situ synthesis of the probe on appropriately derivatized glass or alternate support, or via post-synthetic attachment of the probe to an appropriate solid support. In situ synthesis of arrays entails direct synthesis of a large number of oligonucleotides directly, and often in parallel, on a surface such as a glass slide or silicon chip.

Postsynthetic attachment entails the automated synthesis of all the component oligonucleotides of an array such that they all bear a reactive site on their structure. Reaction at this site with an appropriate functional group and location on the desired solid support affords following multiple attachment reactions an oligonucleotide array.

Post-synthetic attachment of oligonucleotides allows for the synthesis of the probes via conventional nucleic acid chemistry modification of duplex stability via alterations in the length of the probe used, and superior loading densities.

The present invention provides methods to validate a gene and its product as a potential drug target (Glasser, *Genetic Engineering News*, 1997, 17, 1). This process, i.e., confirming that modulation of a gene that is suspected of being involved in a disease or disorder actually results in an effect that is consistent with a causal relationship between the gene and the disease or disorder, is known as target validation.

Efforts such as the Human Genome Project are yielding a vast number of complete or partial nucleotide sequences, many of which might correspond to or encode targets useful for new drug discovery efforts. The challenge represented by this plethora of information is how to use such nucleotide sequences to identify and rank valid targets for drug discovery. Antisense technology provides one means by which this might be accomplished. Superior target specificity that is characteristic of antisense compounds makes them ideal choices for target validation, especially when the functional roles of proteins that are highly related are being investigated (Albert et al., *Trends in Pharm. Sci.*, 1994, 15, 250).

To this end, aminooxy functionalized oligonucleotides are used in methods directed to target validation. The oligomers of the present invention are used to confirm that modulation of a gene that is thought to be involved in a disease or disorder will, in fact, cause an in vitro or in vivo effect indicative of the origin, development, spread or growth of the disease or disorder. The oligomers of the present invention are contacted with a cell culture, cell-free extract, tissue or animal capable of expressing the gene of interest, and subsequent biochemical or biological parameters indicative of the origin, development, spread or growth of the disease or disorder are measured. These results are compared to those obtained with a control cell system, cell-free extract, tissue or animal which has not been contacted with an oligomer of the invention in order to determine whether or not modulation of the gene of interest will have a therapeutic benefit or not. The resulting oligomers may be used as positive controls when other, non antisense-based agents directed to the same target nucleic acid, or to its gene product, are screened.

While antisense drug discovery naturally requires that the toxicity of the antisense compounds be manageable, for target validation, overt toxicity resulting from the oligomers is acceptable unless it interferes with the assay being used to evaluate the effects of treatment with such oligomers.

Formulation of therapeutic compositions utilizing compounds of the present invention and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to about 10 g per kg of body weight, once or more daily, to once every 20 years.

Additional objects, advantages and novel features of the present invention will become apparent to those skilled in the art upon examination of the following examples. The following examples illustrate the invention and are not intended to limit the same. Those skilled in the art will recognize, or be able to ascertain through routine experimentation, numerous equivalents to the specific substances, compositions and procedures described herein. Such equivalents are considered to be within the scope of the present invention.

EXAMPLES

In general, the reagents used in oligonucleotide synthesis were purchased from commercial sources (including one or more of: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). Aldehyde-derivatized Tentagel supports were from Rapp Polymere Gmbh, Tubingen, Germany, and the epoxy-modified microparticles were from SINTEF Applied Chemistry, Trondheim, Norway. Other reagents were readily available from Aldrich Chemical Co., Milwaukee, Wis. Adsorption chromatography was performed on silica gel 60 (Merck). NMR spectra were recorded on Jeol GX-400 spectrometer operating at 399.8 and 100.5 MHz for $^1$H and $^{13}$C, respectively and 161.9 MHz for $^{31}$P. CDCl$_3$ and DMSO-d$_6$ were used as solvents, and TMS as an internal ($^1$H) standard and H$_3$PO$_4$ as an external ($^{31}$P) standard. Electron spray ionization mass spectra were recorded with PE SCIEX API 365 LC/ESI-MS/MS. UV-measurements were carried out on a Perkin-Elmer Lambda 2 UV/VIS-spectrometer.

Analytical TLC was conducted on silica gel 60 F$_{254}$ plates (Merck). Eluent systems: A (1:49, MeOH:CH$_2$Cl$_2$, v/v); B (1:19, MeOH:CH$_2$Cl$_2$, v/v); C (1:9, MeOH:CH$_2$Cl$_2$, v/v); D (3:2, n-hexane:CH$_2$Cl$_2$, v/v); E (17:34:49, Et$_3$N:MeOH:CH$_2$Cl$_2$, v/v/v); F (1:4, n-hexane:CH$_2$Cl$_2$, v/v); G (1:2:7, Et$_3$N: eOH:CH$_2$Cl$_2$, v/v/v).

Oligonucleotides were analyzed by ion exchange chromatography (column: Synchropak AX-300, 4.0×250 mm, 6 μm), flow rate 1 mL min$^{-1}$, buffer A=0.05 KH$_2$PO$_4$ in 50% (v/v) formamide, pH=5.6; buffer B=A+0.6 mol L$^{-1}$ (NH$_4$)$_2$SO$_4$, linear gradient from 10 to 80% B in 30 minutes. The reversed-phase conditions (also LC/ESI-MS/MS) were: column: Nucleosil C18, 300, 4.6×250 mm, 5 μm), linear gradient from 5 to 60% B in 30 minutes and from 60 to 100% B from 30 to 50 minutes, flow rate 1 mL min$^{-1}$, buffer A=0.05 M aq. NH$_4$OAc, buffer B: A in 65% MeCN.

Protected oligonucleotides were assembled on an Applied Biosystems 392 DNA Synthesizer in 0.2 and 1.0 pmol scales using commercial solid supports and phosphoramidite chemistry. Phosphoramidites: O-(11-phthalimidooxy -3,6,9-trioxaundecyl)-O-(2-cyanoethyl)-(N,N-diisopropyl) phosphoramidite; 2'-deoxy-5'-O-(4,4'-dimethoxytrityl)-N$^4$-(5-phthalimidooxypentyl)cytidine 3'-[O-(2-cyanoethyl)-N, N-diisopropyl)]phosphoramidite; and 5'-O-(4,4'-Dimethoxytrityl)-2'-O-(2-phthalimidooxyethyl)-5-methyluridine 3 '-[O-(2-cyanoethyl)-N,N-diisopropyl)] phosphoramidite were used as 0.1 molar solutions in dry MeCN, with a coupling time of 600 seconds, otherwise unaltered and recommended synthesis protocols were used.

After synthesis, the support bound oligonucleotides were first treated with 0.5 mol L$^{-1}$ hydrazine hydrate in Py/AcOH (4:1 v/v) for 30 minutes and then with ammonia for 8 hours at 55° C.

Example 1

Synthesis of 11-(4,4'-dimethoxytrityloxy)-3,6,9-trioxaundecanol (4)

Tetraethyleneglycol (14.0 g, 72 mmol) was coevaporated with dry pyridine (2×50 mL), dissolved in dry dioxane and 4,4'-dimethoxytrityl chloride (8.0 g, 23.6 mmol) was added portion-wise to the stirred solution. The reaction was monitored by TLC. After overnight stirring at ambient temperature, the reaction mixture was evaporated and dissolved in CH$_2$Cl$_2$ (200 mL), and washed with saturated aq. NaHCO$_3$ (3×100 mL) and brine (100 mL). The organic phase was dried over Na$_2$SO$_4$ and concentrated. Purification on silica gel column using a stepwise gradient of MeOH (0 to 10%) in H$_2$Cm$_2$ containing 0.2% pyridine yielded 8.5 g (73%) of the title compound.

$^1$H NMR (CDCl$_3$): δ=7.25–7. 45 (9H, m, DMTr, 6.81 (4H, d, J=8.8, DMTr), 3.77 (6H, s, 2×OMe), 3.70–3.65 (12H, m 3×OCH$_2$CH$_2$), 3.59 (2H, m, HOCH$_2$—), 3.23 (2H, t, J=5.4, DMTrOCH$_2$—); $^{13}$C NMR (CDCl$_3$): δ=158.3, 145.0, 136.3, 130.0, 129.0, 128.2, 127.7, 126.6, 125.2, 113.0, 85.9, 72.5, 70.3–70.7 (5'C), 63.1, 61.7, 55.1 (2'C). TLC: R$_f$(B)=0.4.

Example 2

Synthesis of N-[11-(4,4'-Dimethoxytrityloxy)-3,6,9-trioxaundecanyloxy]phthalimide (5)

N-hydroxyphthalimide (0.7 g, 4.3 mmol) and triphenylphosphine (1.1 g, 4.2 mmol) were added to a solution of 11-(4,4'-dimethoxytrityloxy)-3,6,9-trioxaundecanol (2.0 g, 4.0 mmol) in THF (60 mL). Diethylazodicarboxylate (DEAD, 0.7 mL, 3.6 mmol) was added dropwise and the stirring was continued overnight at ambient temperature. The reaction mixture was evaporated to an oil, applied onto a silica gel column, and eluted with a linear gradient from neat CH$_2$Cl$_2$ to a 97:3 (v/v) mixture of CH$_2$Cl$_2$ and MeOH. The purification was repeated to yield 2.1 g (80%) of the title compound.

$^1$H NMR (CDCl$_3$): δ=7.70–7.85 (4H, m, phthaloyl), 7.45–7.25 (9H, m, DMTr), 6.80 (4H, d, J=9.0, DMTr), 4.35 (2H, t, J=4.6, DMTrOCH$_2$), 3.84 (2H, t, J=4.6, DMTrOCH$_2$CH$_2$), 3.77 (6H, s, 2×OMe), 3.70–3.55 (10H, m, 5×CH$_2$), 3.21 (2H, t, J=5.4, CH$_2$ON). $^{13}$C NMR (CDCl$_3$): δ=163.41, 158.38, 149.82, 145.10, 137.85, 136.35, 134.39, 130.06, 129.00, 182.22, 127.73, 126.64, 125.29, 123.45, 113.03, 85.91, 77.17, 70.81, 70.70, 70.66, 70.58, 69.34, 63.13, 55.19. TLC: R$_f$(B)=0.9.

Example 3

Synthesis of O-(11-phthalimidooxy-3,6,9-trioxaundecyl)-O-(2-cyanoethyl)-(N,N-diisopropyl) phosphoramidite A solution of dichloroacetic acid in CH$_2$C$_{32}$ (100 mL, 3:97, v/v) and methanol (20 mL) was added to N-[11-(4,4'- dimethoxytrityloxy)-3,6,9-trioxaundecanyloxy]phthalimide (2.3 g, 3.6 mmol), and the reaction mixture was stirred for 18 hours. All volatile material was evaporated in vacuo and the residue was dissolved in $CH_2Cl_2$ (10 mL). Silica gel column purification using an eluent system with a stepwise gradient of acetic acid in $CH_2Cl_2$ (0–4%) gave 0.88 g (72%) of 11-(phthalimidooxy)-3,6,9-trioxaundecan-1-ol after coevaporation of the pooled fractions with water and pyridine.

$^1$H NMR ($CDCl_3$): δ=7.90–7.75 (4H, m, phthaloyl), 4.39 (2H, t, J=4.6, H-11), 3.87 (2H, t, J=4.6, H-10), 3.90–3.50 (12H, m, 3×$OCH_2CH_2$). TLC: $R_f$(B)=0.3.

The resulting alcohol (0.37 g, 1.09 mmol) was further dried by coevaporation with dry MeCN and finally in vacuo. 2-Cyanoethyl-N,N,N',N'-tetraisopropylphosphorodiamidite (0.45 mL, 1.42 mmol), MeCN (1.0 mL) and 1H-tetrazole (0.45 mol L$^{-1}$, 2.43 mL, 1.10 mmol) were added and the reaction mixture was stirred at ambient temperature. After 60 minutes, 100 mL of saturated aqueous $NaHCO_3$ solution was added and the mixture was extracted with ethylacetate (3×50 mL). The organic phase was dried with $Na_2SO_4$, and evaporated to give 0.58 g (98%) of the title compound.

$^1$H NMR ($CDCl_3$): δ=d, ppm): 7.90–7.75 (4H, m, phthaloyl), 4.38 (2H, t, J=4.6, H-11), 3.87 (2H, t, J=4.6, H-10), 3.90–3.50 (16H, 3×$OCH_2CH_2$, $POCH_2$ and 2×PNCH), 2.66 (2H, t, J=6.6, $CH_2CN$), 1.30–1.10 (12H, 4×$CH_3CHN$). $^{31}$P NMR($CDCl_3$): 147.63. TLC: $R_f$(B)=0.3.

Example 4

Synthesis of $N^4$-benzoyl-2'-deoxy-5'-O-(4,4'-dimethoxytrityl)-cytidine (6)

2'-Deoxycytidine (5.82 g, 25.6 mmol) was dried by evaporation with dry pyridine (2'50 mL) and taken up in dry pyridine (100 mL). To this suspension, trimethylsilyl chloride (11.5 mL, 90.6 mmol) was added and the mixture was stirred at ambient temperature for 2 hours. The reaction mixture was cooled using an ice water bath and benzoyl chloride (4.60 mL, 39.6 mmol) was slowly introduced. The ice-water bath was removed and the mixture was stirred at room temperature for an additional 2 hours. The reaction was quenched by adding methanol (15 mL), concentrated to one half of the original volume and filtered. To the filtrate, water (30 mL) was added and the solution was evaporated to an oil. Additional evaporations with water (3×30 mL) were performed to remove pyridine, and the resulting residue was partitioned between water and ethyl acetate. After vigorous stirring, the product crystallized from the aqueous layer. The crystals were washed with cold water and ethyl acetate, and they were used in the next step without further purification. TLC: $R_f$(B)=0.7. Crude $N^4$-benzoyl-2'-deoxycytidine was dried by evaporation with dry pyridine (3×50 mL), and then dissolved in the same solvent (100 mL). 4,4'-Dimethoxy-tritylchloride (7.4 g, 22 mmol) was added portion-wise to the reaction mixture, and the stirring was continued overnight at ambient temperature. The reaction mixture was evaporated to an oil and dissolved in $CH_2Cl_2$ (100 mL). The organic phase was washed with saturated aqueous $NaHCO_3$ (50 mL) and water (3×100 mL), and dried with anhydrous $Na_2SO_4$. After coevaporation with toluene, the residue was applied onto a silica gel column and eluted with a gradient of MeOH in $CH_2Cl_2$ (0–8% MeOH). The title compound (6) was obtained in 65% yield (9.0 g) starting from 2'-deoxycytidine.

$^1$H NMR ($CDCl_3$): δ=d, ppm): 8.30 (1H, d, J=7.6, H-6), 7.45–7.10 (9H, m, DMTr), 6.84 (4H, m, DMTr), 7.90–7.40 (5H, m, benzoyl), 6.31 (1H, t, J=5.9, H-1'), 4.55 (1H, m, H-3'), 4.19 (1H, m, H-4'), 3.78 (6H, s, 2×OMe), 3.49 (1H, dd, J=3.2 and 11.0, H-5'), 3.42 (1H, dd, J=3.9 and 10.8, H-5"), 2.77 (1H, m, H-2"). TLC: $R_f$(C)=0.85.

Example 5

Synthesis of 2'-deoxy-$N^4$-(5-hydroxypentyl)-5'-O-(4,4'-dimethoxytrityl)cytidine (7)

A solution of 5-aminopentanol (10.0 g, 96.9 mmol) in 2-propanol (10 mL) was added to $N^4$-benzoyl-2'-deoxy-5'-O-(4,4'-dimethoxytrityl)cytidine (2.61 g, 4.12 mmol) and stirred until the mixture was clear. 1,5,7-Triazabicyclo[4.4.0]dec-5-ene (TBD, 2.40 g, 17.2 mmol) was added and the reaction mixture was stirred at ambient temperature for 48 hours. The reaction mixture was evaporated to an oil under high vacuum via oil pump, dissolved in $CHCl_3$ (100 mL), extracted with 0.1 molar aqueous NaOH (2×50 mL) and water (4×50 mL). The organic phase was dried with anhydrous $Na_2SO_4$, evaporated, and dissolved in $CH_2Cl_2$. The organic phase was evaporated to an oil and purified by silica gel column chromatography using 2:4:94 $Et_3N$:MeOH:$CH_2Cl_2$ and 2.5:5:92.5 $Et_3N$:MeOH:$CH_2Cl_2$; v/v/v as the eluent. The purification was repeated until a reasonably pure product was obtained. The removal of side product 2'-deoxy-5'-O-(4,4'-dimethoxytrityl)-cytidine was responsible for the necessary of additional purification. After purification 0.53 g (18%) of the title compound was isolated.

$^1$H NMR ($CDCl_3$): δ=7.75 (1H, d, J=7.3, H-6), 7.45–7.15 (9H, m, DMTr), 6.82 (4H, d, J=8.5, DMTr), 6.33 (1H, t, J=5.9, H-1'), 5.40 (1H, d, J=7.3, H-5), 4.49 (1H, m, H-3'), 4.05 (1H, dd, J=3.7, H-4'), 3.77 (6H, s, 2×OMe), 3.60 (2H, t, J=5.9, $CH_2OH$), 3.50–3.30 (4H, m, H-5', H-5", $HNCH_2$), 2.17 (1H, m, H-2'), 1.57 (4H, m, 2×$CH_2$), 1.40 (2H, m, $CH_2$). TLC: $R_f$(E)=0.7.

Example 6

Synthesis of 2'-deoxy-5'-O-(4,4'-dimethoxytrityl-$N^4$-(5-phthalimidooxypentyl)cytidine (8)

To 2'-deoxy-$N^4$-(5-hydroxypentyl)-5'-O-(4,4'-dimethoxytrityl)cytidine, dried by evaporation with dry pyridine (2!20 mL), was added N-hydroxyphthalimide (0.17 g, 1.04 mmol), triphenylphosphine (0.14g, 0.53 mmol) and dry THF (30 mL) was added. Diethyl azodicarboxylate (DEAD, 0.089 mL, 0.57 mmol) was added dropwise and the resulting mixture was stirred at ambient temperature for 18 hours. All volatile material was evaporated in vacuo, and the residue was dissolved in a small volume of $CH_2Cl_2$ and applied onto a silica gel column. Triphenylphosphine oxide was eluted first from the column with a mixture of i-PrOH and $CH_2Cl_2$ (1:19, v/v), and the product was eluted with a mixture of MeOH and $CH_2Cl_2$ (1:9, v/v). The purification afforded 0.24 g (40%) of the title compound.

$^1$H NMR ($CDCl_3$): δ=8.61 (1H, m, NH), 7.85–7.65 (4H, m, phthaloyl), 7.45–7.15 (9H, m, DMTr), 6.83 (4H, m, DMTr), 6.30 (1H, t, H-1'), 5.47 (1H, d, J=7.3, H-5), 4.51 (1H, m, H-3'), 4.21 (2H, t, J=5.9, $CH_2ON$), 4.05 (1H, m, H-4'), 3.78 (6H, s, 2×OMe), 3.60–3.10 (4H, m, H-5',H-5", $CH_2N$), 2.60 (1H, m, H-2'), 2.20 (1H, m, H-2"), 1.79 (2H, m, $CH_2$), 1.70–1.40 (4H, m, 2×$CH_2$). TLC: $R_f$(C)=0.5.

Example 7

2'-deoxy-5'-O-(4,4'-dimethoxytrityl)-$N^4$-(5-phthalimidooxy-pentyl)cytidine 3'-[O-(2-cyanoethyl)-N,N-diisopropyl)]phosphoramidite (2)

To a solution of 2-cyanoethyl-N,N,N',N'-tetraisopropyl-phosphorodiamidite (0.12 mL, 0.38 mmol) and dry acetonitrile (1.0 mL) was added 2'-deoxy-5'-O-(4,4'-dimethoxytrityl-N$^4$-(5-phthalimidooxypentyl)cytidine (0.22 g, 0.29 mmol) dried by coevaporation with dry acetonitrile (3'20 mL) and finally in vacuo for 30 minutes. The resulting mixture was stirred until all material dissolved. 1H-Tetrazole (0.45 molar in MeCN, 0.64 mL, 0.29 mmol) was added, and the reaction mixture was shaken. After one hour at ambient temperature saturated aqueous NaHCO$_3$ solution (100 mL) was added, and the resulting solution was extracted with ethyl acetate (2'40 mL). The organic phase w as dried with anhydrous Na$_2$SO$_4$ and evaporated to dryness, affording 0.24 g (97%) of the title compound.

$^1$H NMR (CDC$_3$): δ=7.75–7.70 (4H, m, phthaloyl), 7.45–7.20 (9H, m, DMTr), 6.83 (4H, m, DMTr), 6.36 (1H, m, H-4'), 5.41 (1H, d, J=5.6, H-5), 4.60 (1H, m, H-3'), 4.22 (2H, t, J=5. 4, CH$_2$ON), 4. 10 (1H, m, H-4') 3. 78 (6H, s, 2×OMe), 3.65–3.30 (8H, m, H-5', H-5", CH$_2$N, POCH$_2$, 2×PONCH), 2. 63 (2H, m, CH$_2$CN), 2.60 (1H, m, H-2'), 2.25 (1H, m, H-2"), 1.85–1.50 (6H, m, 3×CH$_2$), 1.30–1.00 (12H, m, 4×CH$_3$). $^3$P NMR (CDCl$_3$): δ=149.2 and 148.7.

Example 8

5'-O-(4,4'-Dimethoxytrityl)-2'-O-(2-phthalimidooxyethyl)-5-methyluridine 3'-[O-(2-cyanoithyl)-N,N-diisopropyl)]phosphoramidite (3)

The title compound was prepared as per the procedure illustrated in Kawasaki et al., *Tetrahedron Lett.*, 1999, 40, 661–664.

Example 9

1-Phthalimidooxy-hex-5-yne

To 5-Hexyn-1-ol is added N-hydroxyphthalimide (1.1 equivalent) in dry THF. To this mixture is added diethylazodicarboxylate (DEAD) dropwise with stirring at ambient temperature for 18 hours. Evaporation of the reaction mixture followed by silica column purification yielded the 1-phthalimidooxy-hex-5-yne.

Example 10

5-(6-phthalimidooxyhex-1-ynyl)-2'-deoxyuridine

To a suspension of 5-iodo-2'-deoxy-uridine (2 mmol) in CH$_2$Cl$_2$ (10 mL), is added trifluoroacetic anhydride (5 mmol) at room temperature. The mixture is stirred overnight and then concentrated. The resulting material is dried in vacuo at room temperature to give a solid foam of 3',5'-di-O-trifluoroacetyl-5-iodo-2'-deoxyuridine.

To a mixture of 3'-5'-di-O-trifluoroacetyl-5-iodo-2'-deoxyuridine (5 mmol) and N-1-phthalimidooxyhex-5-yne (10 mmol) tetrakis (triphenylphosphine) palladium (0) (0.2 mmol), copper (I) iodide (0.3 mmol) and triethylamine (6 mmol) are added in DMF (10 mL). The mixture is stirred at room temperature for 18 hours and then concentrated under a vacuum. To the concentrate, AG-lx8 anion exchange resin (HCO$_{3-}$ form, 3 equivalents), methanol (20 mL), and CH$_2$Cl$_2$ (20 mL) are added, and the suspension is stirred for 1 hour. The resulting solution is concentrated and the residue is purified by silica gel column chromatography to give the title compound.

Example 11

5'-O-DMT-5-(6-phthalimidooxyhex-1-ynyl)-2'-deoxyuridine 5-(6-phthalimidooxyhex-1-ynyl)-2'-deoxy-uridine is treated with 4,4'-dimethoxytrityl chloride (1.2 eq.) in pyridine containing dimethylaminopyridine (0.1 eq.) with stirring for 4 hours. The pyridine is evaporated and the residue is dissolved in methylene chloride, washed with saturated sodium bicarbonate solution, dried over anhydrous sodium sulfate and concentated. The residue is purified using silica gel column chromatography with ethyl acetate:hexane system as the eluent to give the title compound.

Example 12

5'-O-DMT-5-(6-phthalimidooxyhex-1-ynyl)-uridine-3'-O-[(2-cyanoethyl)N,N-diisopropyl] phosphoramidite 5'-O-DMT-5-(6-phthalimidooxyhex-1-ynyl)-2'-deoxyuridine (1 mmol) is dissolved in dry CH$_2$Cl$_2$ (15 mL) and N,N-diiso-propylammonium tetrazolide (0.5 mmol) is added. To the resulting mixture is added 2-cyanoethyl-N,N,N'N'-tetraisopropyl phosphorodiamidite (1.1 mmol) slowly via syringe under argon. The mixture is stirred at room temperature overnight, after which the progress of the reaction is checked using TLC (CH$_2$Cl$_2$:EtOAc 50:50). An additional aliquot of the phosphitylation reagent (0.12 mmol) is added and the mixture stirred for an additional 2 hours. The progress of the reaction is again checked using TLC. If the conversion is complete by TLC the reaction mixture is diluted with 50 mL CH$_2$Cl$_2$ and washed with saturated NaHCO$_3$ solution followed by saturated NaCl solution. The organic layer is dried over MgSO$_4$ and evaporated to dryness. The resulting crude foam is purified by chromatography on silica gel and eluted with 50:50 EtOAc:CH$_2$Cl$_2$ to give the title phosphoramidite.

Example 13

5'-O-DMT-N$^4$-benzoyl-5-(6-phthalimidooxyhex-1-ynyl)-2'-deoxycytidine-3'-O-[(2-cyanoethyl) N,N-diisopropyl]phosphoramidite To 5-iodo-2'-deoxycytidine (5 mmol), tetrakis (triphenylphosphine) palladium (0) (0.5 mmol), copper (I) iodide (1 mmol) and N-1-phthalimidooxy-hex-5-yne (12 mmol) in dry DMF (15 mL), triethylamine (10 mmol) is added. After stirring for 18 hours, AG-lx8 anion exchange resin (HCO$_3^-$ form, 3 equivalents), methanol (20 mL), and CH$_2$Cl$_2$ (20 mL) are added, and the suspension is stirred for 1 hour. The reaction is filtered through a sintered glass funnel, and the DMF removed in vacuo. Flash chromatography yielded the product C5 substituted nucleoside. The C5 substituted nucleoside was further treated with benzoic anhydride (one equivalent) in dry pyridine to give N-4-benzoyl derivative. The N-4-benzoyl derivative was converted into the DMT phosphoramidite, e.g. the title compound following the procedure of Example 4.

Example 14

1-t-Butyldiphenylsilyl-6-aminohexanol 1,6-Hexanediol is monosilylated with tert-butylchlorodiphenylsilane (1 equivalent) in dry pyridine. It is then mesylated with mesyl chloride in pyridine and subsequently treated with lithium azide in DMF solvent. The resulting azide derivative is reduced with triphenyl phosphine to give the title compound.

Example 15

5'-o-DMT-2-(6-phthalimidooxy-aminohexyl)-2'-deoxyadenosine-3'-O-[(2-cyanoethyl)N,N-diisopropyl]phosphoramidite 2-Fluoroadenosine is synthesized according to a previously reported procedure (Krolikiewicz et al., *Nucleosides*

*and Nucleotides,* 1994, 13, 673). 1-t-BuDPS-6-aminohexanol (5 equivalents, in 2-methoxyethanol) is added to 2-fluoroadenosine and heated at 100°. The resulting 2-(aminohexanol)-derivative is treated with benzoyl chloride under transient protection conditions followed by treatment with dimethoxytritylchloride as per the procedures illustrated in Example 13. The silyl protecting group is removed by treatment with tetrabutyl ammonium fluoride and the resultant nucleoside is subjected to Mitsunobu reaction with $Ph_3P$, N-hydroxyphthalimide and diethylazodicarboxylate (DEAD). The resulting compound is then phosphitylated follwing the procedures described above to give the title compound.

Example 16

5'-O-DMT-2-(6-phthalimidooxy-aminohexyl)-2'-deoxyinosine-3'-O-[(2-cyanoethyl)N,N-diisopropyl]phosphoramidite 2-fluoroinosine is synthesized according to a previously reported procedure (Krolikiewicz, ibid). 1-t-BuDPS-6-aminohexanol (5 equivalents, in 2-methoxyethanol) is added to 2-fluoroinosine and heated at 100°. The nucleoside is treated with dimethoxytritylchloride and then the silyl protecting group is removed by treatment with tetrabutyl ammonium fluoride. The resultant nucleoside is subjected to Mitsunobu reaction with $Ph_3P$, N-hydroxyphthalimide, and diethylazodicarboxylate (DEAD). The resulting compound is then phosphitylated follwing the procedures described above to give the title compound.

Example 17

5'-O-DMT-N2-isobutyryl-N6-(6-phthalimidooxy-hexyl)-2'-deoxy-adenosine-3'-O-[(2-cyanoethyl)N,N-diisopropyl]phosphoramidite To 2'-deoxyguanosine (2 mmol), dried by coevaporation with pyridine, suspended in pyridine (40 mL) and cooled in an ice bath under an argon atmosphere, trifluoroacetic anhydride (16 mmol) is added (as per the procedure of: Kung, et al., *Tetrahedron Lett.,* 1991, 32, 3919). After 40 minutes, 1-t-Butyldiphenylsilyl-6-aminohexanol (30 mmol) is added and stirred for 24 hours at room temperature. The reaction mixture is concentrated and purified by silica gel column chromatography. The product is protected at the N2-position with an isobutyryl group via treatment with isobutyric anhydride and further protected by treatment with dimethoxytritylchloride and purified. The silyl protecting group is removed by treatment with tetrabutyl ammonium fluoride and the resultant nucleoside is subjected to a Mitsunobu reaction with $Ph_3P$ and N-hydroxyphthalimide with diethylazodicarboxylate (DEAD). The resulting compound is treated with benzoic anhydride (N6 protection) and then phosphitylated follwing the procedures described above to give the title protected phosphoramidite.

Example 18

Conjugation of Oligonucleotides to Microparticles

Oligonucleotides incorporating aminooxy functional groups either indirectly attached to the 5'-O-position (SEQ ID NO: 1) or attached to an exocyclic amino functionality of a heterocyclic base (SEQ ID NO: 2) were prepared by standard phosphoramidite protocols using compounds 3 and 7 respectively. A modified coupling time of 600 seconds was used to insert the compounds 3 and 7 for their respective oligonucleotides. Deprotection and cleavage was performed with a double syringe method employing a 0.5 molar hydrazine acetate solution (0.124:4:1 $H_2NNH_2H_2O$: Pyridine:AcOH, v/v/v) for 30 minutes, followed by treatment with concentrated ammonia at 55° C. for 8 hours. Although this treatment has previously been used in solid-phase oligonucleotide synthesis (Azhayev et al., *Tetrahedron Lett.,* 1993, 34, 6435–6438), we checked the effect on each nucleoside separately. A sample of each CPG-bound nucleoside (dA, dG, dC and T) was treated according to the deprotection protocol and analyzed by RP-HPLC. No additional peaks were detected in the chromatograms of the hydrazine treated nucleosides compared to those referring to nucleosides released from the support by mere ammonolysis.

The crude oligonucleotides were evaporated to dryness and dissolved in water (1.0 mL) and mixed immediately with aldehyde derivatized microparticles (90 nmol of SEQ ID NO: 1 and 2.8 mg Tentagel, 0.6 µmol CHO-groups, or 80 nmol of SEQ ID NO: 2 and 3.5 mg Tentagel, 0.8 µmol CHO-groups). SEQ ID NO: 2 (1.0 mL, 80 nmol) was also conjugated to epoxide-modified microparticles (3.0 mg, 0.3 mmol epoxide-groups). The resulting conjugate is similar to the one shown below for SEQ ID NO: 2 with a different terminal linkage to the microparticle e.g. —O—N (H)—$CH_2$—C (H) (OH)-microparticle. The progress of the reactions were followed by UV-absorbance change at 260 nm. According to the observed decrease in the absorbance, a loading of 1 µmol of oligonucleotides in one gram of the microparticles was obtained.

9, SEQ ID NO: 1 5'-dA*CA CCA AAG ATG ATA T

10, SEQ ID NO: 2 5'-dACA CCA AAG ATG ATA TC**T

*=5'—O—P(=O) (—OH)—O—($CH_2CH_2$—O)$_4$—$NH_2$; and

**=$N^4$—($CH_2$)$_5$—O—$NH_2$

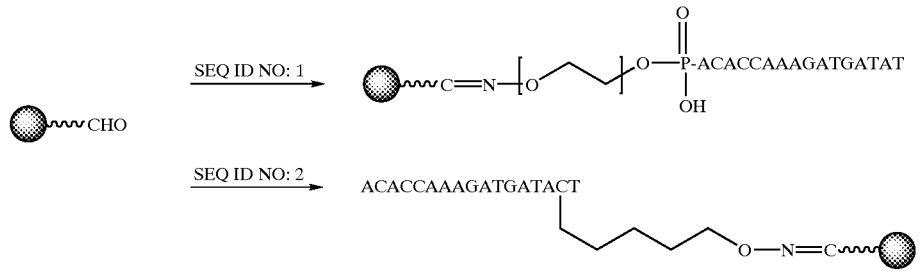

Following synthesis, the microparticle conjugated oligonucleotides were washed with water and dried. The dried microparticles were used in hybridization assays as illustrated below.

Example 19
Hybridization Assays

Microparticle conjugated oligonucleotides (SEQ ID NOs: 1 and 2, Example 18) were used as capture probes for a complementary oligonucleotide 16-mer (SEQ ID NO: 3) having a tethered photoluminescent europium(III) chelate (Mukkala et al., *Helv. Chim. Acta.*, 1993, 76, 1361–1378). A non-complementary oligonucleotide (SEQ ID NO: 4) was prepared also having a tethered photoluminescent europium (III) chelate to study the percentage of unspecific binding to the solid phase.

SEQ ID NO: 3 5'-dX$_5$ ATA TCA TCT TTG GTG T

SEQ ID NO: 4 5'-dX$_5$ TCA TGA GTC AAG TCT A

X=N$^4$-(6-aminohexyl)-2'-deoxycytidine tethered to a photoluminescent europium(III) chelate, {2,2',2",2'''-{{4'-{4'''-[(4,6-dichloro-1,3,5-triazin-2-yl)amino]phenyl}-2,2':6',2"-terpyridine-6,6"-diyl}bis(methylenenitrilo)}-tetrakis (acetato)}europium(III).

The signal intensity of time-resolved fluorescence of the europium from one microparticle was measured with a microfluorometer as a function of each added oligonucleoide (SEQ ID NOs: 3 and 4). Measurements and hybridization protocols were performed as illustrated in: Hakala et al., *Bioconjugate Chem.*, 1998, 9, 316–321; Hakala et al., *Bioconjugate Chem.*, 1997, 8, 232–237; and Lovgren et al., *Clin. Chem.*, 1997, 43, 1937–1943. With the aldehyde-derivatized Tentagel, a slightly modified mode of measurement was applied. Instead of capillary tubing, the microparticles were collected on a filter and the signal was collected from one bead with the microfluorometer.

According to the measurements, the intensity of the fluorescence emission signal obtained on treating the particles with a complementary fluorescently tagged oligonucleotide (SEQ ID NO: 3) was always more than two orders of magnitude higher than that resulting from unspecific binding of a noncomplementary fluorescently labeled oligonucleotide (SEQ ID NO: 4) to the particles. The following systems were tested: (i) oligonucleotide conjugate SEQ ID NO: 1 immobilized to aldehyde-coated Tentagel, (ii) conjugate SEQ ID NO: 2 immobilized to aldehyde-coated Tentagel, and (iii) conjugate SEQ ID NO: 2 immobilized to epoxide-coated polyacrylate particles. The epoxide-modified microparticles exhibited a somewhat higher ratio of specific to unspecific binding signal than the aldehyde derivatized Tentagel particles.

Example 20
Post Synthesis Conjugation of Oligonucleotides

Figure 15:
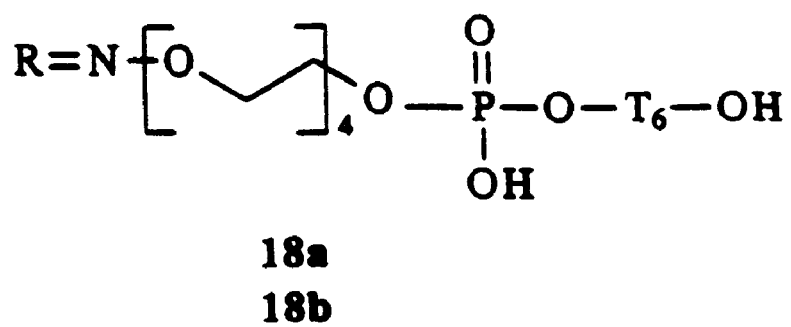
FIG. 15 shows the structures of compounds 18a, 18b, 19a and 19b.
Figure 15:
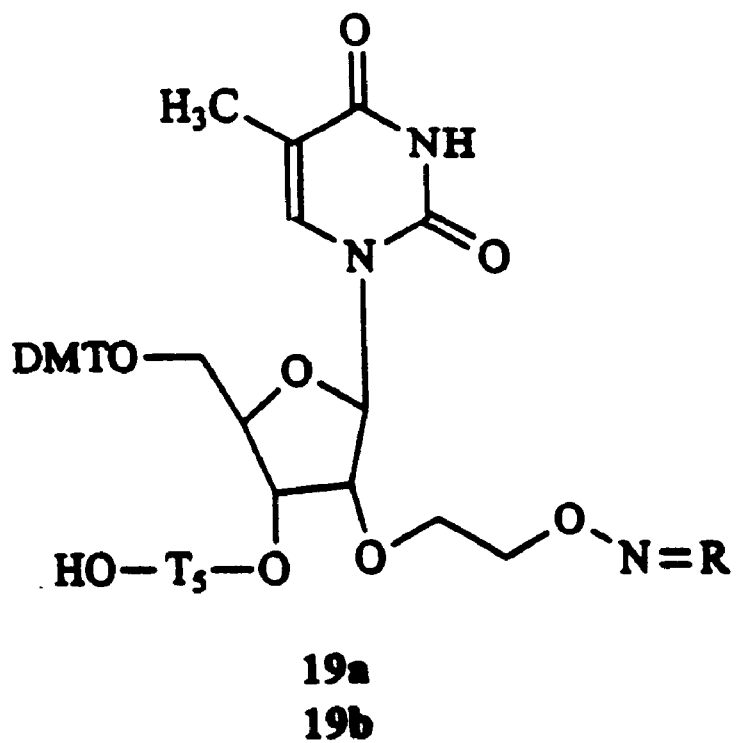

Two 6-mer oligonucleotides were prepared using CPG-succinyl-thymine and phosphoramidite protocols for solid phase synthesis. Using compound 1 for the final coupling the sequence 5'-T*T$_5$ (18) was prepared where T* is 5'—O—P(=O) (—OH)—O—(CH$_2$CH$_2$—O)$_4$—NPhth—T. Using compound 8 (Example 6) for the final coupling the sequence 5'-[(2'-O-pentyloxyphthaloyl)-5-methyl]-UT$_5$ (19) was prepared. Support-bound oligonucleotides were treated with 0.5 molar hydrazine acetate solution (0.124:4:1 H$_2$NNH$_2$.H$_2$O: Pyridine:AcOH, v/v/v) for 30 minutes and washed with pyridine, methanol, acetonitrile then dried. The supports (2.0 mg/sample, 50 nmol of ODN) were transferred to microcentrifuge tubes and treated with a solution of either pyrenecarbaldehyde (100 µL, 40 µmol in DMF) or cis-retinal (100 µL, 3.5 µmol in MeCN). The resulting mixtures were shaken for 16 hours, in the dark, at ambient temperature. Excess reagents were removed via subsequent washes with several portions of DMF and MeCN until no color was released from the supports upon further washing. The supports were dried and treated with concentrated ammonia at ambient temperature for 24 hours to release the resulting oligonucleotide-oxime conjugates 18a, 18b, 19a and 19b (a=pyrenyl, b=retinolyl) shown in FIG. 15.

Evaporation, dissolution in water and analysis by HPLC/ESI-MS/MS verified the formation of th e expected oligonucleotide conjugates and complete disappearance of the starting material.

TABLE 1

| Oligo | Retention Time (min) | Observed Mass | Calculated Mass | Product Ratio (%) |
|---|---|---|---|---|
| 18a | 27.9 | 2246.4 | 2246.6 | 41 |
| 18b | 41.8 | 2301.2 | 2300.8 | 51 |
| 19a | 36.7/37.4$^a$ | 2352.6 | 2356.9 | 70 |
| 19b | 38.3 | 2104.4 | 2104.8 | 52 |

$^a$= E/Z isomers, both peaks exhibit same molecular mass.

Example 21
Synthesis of Pentafluorophenyl Ester of 4-pentenoic Acid 4-pentenoic acid (Aldrich) is treated with pentafluorophenol and N,N-dicyclo hexylcarbodiimide (DCC) (1 equivalent each) in dioxane solvent and stirred overnight. The resulting N-N-dicyclohexyl urea (DCU) is filtered off and the solid residue is washed with methylene chloride (CH$_2$Cl$_2$) The combined solution is evaporated and the resultant ester is purified in a silica gel chromatographic column.

Example 22
Coupling of Olefinic group at the Amino Terminal of the Zn-finger Peptide The 30-mer Zn-finger peptide is built using standard peptide synthesis protocol. The final amino residue is deprotected and coupled with pentafluorophenyl ester of 4-pentenoic acid. This gives an olefinic double bond functionality at the amino terminus of the peptide. This peptide with th e olefin tether is then cleaved from the resin and purified. The peptide is characterized by mass spectral and amino acid analysis.

Example 23
Synthesis of Oligonucleotides with —O—NH$_2$ Linker ("O—N linker") N-(1-hydroxyphthalimido)-5-hexene To a stirred solution of 5-hexane-1-ol (20 g, 0.2 mol) in THF (500 mL) was added triphenylphosphine (80 g, 0.3 mol) and N-hydroxyphthalimide (49 g, 0.3 mol). The mixture was cooled to 0° C. and diethylazido carboxylate (48 mL, 0.3 mol) was added slowly over a period of 1 hour. The reaction mixture was allowed to warm to room temperature and the yellow solution was stirred overnight. The solvent was then evaporated to give a yellow oil. The oil was dissolved in CH$_2$Cl$_2$ and washed with water, saturated NaHCO$_3$ solution followed by a saturated NaCl solution. The organic layer was concentrated in vacuo and the resulting oil was dissolved in a solution of CH$_2$Cl$_2$/ether to crystallize out Ph$_3$P=O as much as possible. After three steps of purification the title compound was isolated as a yellow waxy solid (yield 93%). 13C NMR: d 21.94, 24.83, 27.58, 33.26,. 78.26, 114.91, 123.41, 128.40, 128.54, 128.63, 134.45 and 163.8 ppm.

Example 24
Synthesis of N-(1-hydroxyphthalimido-5,6-hexane-diol)

N-(1-hydroxyphthalimido)-5-hexane (2.59 g, 10 mmol), aqueous osmium tetroxide (0.15 M, 3.6 mL, 0.056 mmol)

and N-methylmorpholine-N-oxide (2.46 g, 21 mmol) were dissolved in THF (100 mL). The reaction mixture was covered with aluminum foil and stirred at 25° C. for 4 hours. TLC indicated the diol was formed. The solvent was evaporated and the residue was partitioned between water and $CH_2Cl_2$. The organic layer was washed with a saturated solution of NaCl and dried over anhydrous $MgSO_4$. Concentration of the organic layer resulted in a brownish oil that was characterized by $^{13}C$ NMR and used in the next step without further purification. $^{13}C$ NMR: d 21.92, 28.08, 32.62, 66.76, 71.96, 78.33, 123.43, 128.47, 128.71, 131.93, 132.13, 134.49, 163.89.

Example 25

Synthesis of N-1-hydroxy phthalimido-6-O-dimethyoxytrityl-5,6 Hexanediol

The product from the previous step (3.0 g) was coevaporated with pyridine (2×20 mL) and dissolved in pyridine (100 mL). Dimethoxytrityl chloride (3.5 g, 10 mmol) was dissolved in of pyridine (30 mL) and added to the diol dropwise over a period of 30 minutes. After 4 hours, the reaction was quenched with methanol (10 mL). The solvent was evaporated and the residual product portioned between saturated sodium bicarbonate solution and $CH_2Cl_2$ (100 mL each). The organic phase was dried over anhydrous $MgSO_4$, concentrated and the residue was subjected to silica gel flash column chromatography using hexanes-ethyl acetate-triethyl amine (60:39:1). The product containing fractions were combined, concentrated in vacuo and dried to give a yellow foamy solid. NMR analysis indicated the title compound as a pure homogenous dimethoxytritylated solid (5.05 g, 83% yield).

Example 26

Synthesis of O—N Linker Phosphoramidite

The compound from the previous step was phosphitylated (1.5 g, 2.5 mmol) in $CH_2Cl_2$ solvent (20 mL) by the addition of diisopropylamine tetrazolide (214 mg, 1.25 mmol) and 2-cyanoethyl-N,N,N,N-tetraisopropyl phosphorodiamidite (1.3 mL, 4.0 mmol). After stirring the solution overnight the solvent was evaporated and the residue was applied to silica column and eluted with hexanes-ethyl acetate-triethylamine (50:49:1). Concentration of the appropriate fractions gave 1.61 g of the phosphitylated compound as a yellow foam (81%).

Example 27

Attachment of O—N Linker to CPG

Succinylated and capped CPG was prepared according to method described Damha et al., *Nucleic Acids Res.,* 1990, 115, 7128. Compound containing the O—N linker (0.8 mmol), dimethylaminopyridine (0.2 mmol), 2.0 g of succinylated and capped CPG triethylamine (160 microL) and DEC (4.0 mmol) were shaken together for 24 hours. Pentachlorophenol (1.0 mmol) was then added and the resulting mixture was shaken for 24 hours. The CPG beads were filtered off and washed thoroughly with pyridine (30 mL) dichloromethane (2×30 mL), $CH_3OH$ (30 mL) in ether. The CPG solid support was dried over $P_2O_5$ and its loading was determined to be 28 micromols/g.

Example 28

Synthesis of Oligonucleotides Containing O—N Linker

The following oligonucleotides are synthesized using O—N linker (X):

| | |
|---|---|
| Oligomer No:3 | 5'-X-TCT GAG TAG CAG AGG AGC TC-3' |
| (SEQ ID NO:5) | (2'-MOE, P=O; 11158 analog; ICAM-1 target) |
| Oligomer No:4 | 5'-(TC)$^a$ (CGTCATCGCT)$^b$ (CCTCAGGG)$^a$-X-3' |
| (SEQ ID NO:6) | (Gapmer, 2503 analog, H-ras target) |

$^a$= nucleotides having a 2'-MOE substituent and phosphorothioate linkages;
$^b$= 2'-deoxy nucleotides having phosphorothioate linkages.

These oligonucleotides are synthesized either as phosphodiester (oligomer 3) or as a phosphorothioate (oligomer 4). For the synthesis of oligomer 3, the phosphoramidite compound is used as a 0.2 M solution in $CH_3CN$. The coupling efficiency of ON-linker is optimized to be >95% as can be evaluated by trityl colors. The oligonucleotides were deprotected from the solid support using hydrazinium acetate solution as described in previous examples to generate the free —O—$NH_2$ linker for conjugation. Alternatively the oligomer is left in the solid support to carry out the conjugation in the solid support itself after generating the linker.

Example 29

Generation of Peptide Aldehyde from Peptides with Olefinic Tethers and Conjugation of Peptide to Oligonucleotide via an Oxime Linkage The peptides with olefinic tethers generated in Example 2 are ozonolyzed to yield aldehydes. Alternatively, the peptide with olefinic linker at the amino end is treated with $OsO_4$/NMMO followed by $NaIO_4$. This gives a free aldehyde tether at the amino end of the peptide. This peptide is treated with oligonucleotides containing O—N linker. The —O—$NH_2$ group in the oligonucleotide is generated by $NH_4OH$ deprotection of the synthesized material in the previous step in solution or methylhydazine deprotction in solid support. After allowing the conjugation reaction to proceed to completion, the oxime-linked oligonucleotide is purified by anion-exchange resin.

Example 30

Conjugation of Peptide to Oligonucleotides Using O—N-linker

Oligonucleotide NO:3 in CPG (1 micromol) is taken in a glass funnel reactor and hydrazinium acetate solution is added. The reactor is shaken for 10 minutes. The methyl hydrazine is drained, washed with $CH_2Cl_2$ and the methyl hydrazine reaction was repeated. The beads were washed with $CH_2Cl_2$ followed by ether and dried. Peptide with an aldehyde linker in DMF (5 mL) is added. After shaking for 2 hours, the peptide solution is drained; the oligonucleotide is deprotected in 0.1N NaOH overnight at room temperature. The aqueous solution is then filtered and an HPLC analysis is run. The conjugate product peak had a different retention time than the oligonucleotide and peptide precursors and the diode-array spectrophotometer showed the expected 260/280 absorption.

Example 31

Conjugation of Peptide Aldehyde to Oligonucleotide (SEQ ID NO:4) in Solution

Hydrazinium acetate cleavage of CPG yielded oligonucleotide 4 on solid support with O-amino linker. Peptide aldehyde is added to the oligonucleotide SEQ ID NO:4. The conjugation is allowed to proceed and monitored by reverse phase HPLC. Cleavage of the conjugate product using ammonium hydroxide gave the oligonucleotide conjugate having a different retention time than the oligonucleotide and peptide precursors. The diode-array spectrophotometer showed the expected 260/280 absorption.

Example 32
Synthesis of O-aminolinker Attached Peptide

6-Hydroxycaproic acid is treated with N-hydroxyphthalimide (2 equivalents) and diethyl azodicarboxylate (2 equivalents) at −78° C. is distilled THF solvent. The reaction mixture is warmed to ambient temperature and the solvent is evaporated in vacuo to give a solid residue. The solid residue is purified by silica gel column chromatography to give 6-phthalimidohydroxyhexanoic acid-N-hydroxy-phthalic ester. This compound is coupled to the peptide at the amino terminal. The O—N linker is generated by treating the peptide with 5% methylhydrazine in methylene chloride.

Example 33
Conjugation of Peptide with O—N Linker to Oligonucleotide with Aldehyde Tether The oligonucleotide with olefinic linker is taken in water and treated with $OSO_4$/NMMO followed by $Na_2O_4$. This gives a free aldehyde tether at the tether of the oligonucleotide. This oligonucleotide is then treated with the peptide containing O—N linker from the previous step. After allowing the conjugation reaction to proceed to completion, the oxime-linked oligonucleotide is purified by anion-exchange resin. The conjugate product peak had a different retention time than the oligonucleotide and peptide precursors and the diode-array spectrophotometer showed the expected 260/280 absorption.

Example 34
Synthesis of Biotin-aldehyde Reagent

Biotin is conjugated to 6-aminohexanol using dicyclohexyl carbodiimide reagent in DMF solvent. The resulting alcohol is oxidized to the aldehyde using pyridinium chlorochromate, potassium acetate in methylene chloride at room temperature (according to the procedure of Ducray et al., J. Org. Chem., 1999, 64:3800–3801). The aldehyde compound is purified by silica column chromatography.

Example 35
Detection of Viral Pathogens Using Aminooxy Conjugated Oligonucleotides This example demonstrates the use of aminooxy functionalized oligonucleotides for the detection of HIV in bodily fluid samples of HIV-infected patients. Two oligonucleotides are used in this sandwich hybridization assay. These oligonucleotides are complementary to different regions of the HIV gene. The first oligonucleotide, oligonucleotide-I is attached to microparticles via an aminooxy linkage. The second oligonucleotide, oligonucleotide-II, has several biotin molecules which are derived from a biotin-aminohexanal cojugate.

Oligonucleotide-I has the following sequence, complementary to the TAR region of the HIV genome:

5' *GCC AGA GAG CTC CCA GGC TCA GAT CT 3' (SEQ ID NO:7) This oligonucleotide has an aminooxy linker attached via the N-2 position of G. Oligonucleotide-I is attached to the microparticles as described in the previous examples.

Oligonucleotide-II is complementary to another site on the HIV gene, and has the following sequence:

5' GGT* CTA ACC A*CA GAG A*CCC 3' (SEQ ID NO: 8)

Nucleotides highlighted by an asterisk (*) bear the —O—$NH_2$ linkers at either the C-5 position (T) or N-6 position (A). After synthesis of the oligonucleotides, the aminooxy linkers are generated by hydrazinium acetate treatment. Oligonucleotide-II is treated with an excess of biotin-aminohexanal to form an oligonucleotide-II/biotin conjugate.

The sample to be tested for the presence of HIV is hybridized to oligonucleotide-I (on the solid support), forming an oligonucleotide-I/HIV gene complex. This complex is treated with the oligonucleotide-II/biotin conjugate. This results in the formation of a "sandwich" hybrid which includes oligonucleotide-I, the HIV gene, and oligonucleotide-II. ELISA tests are used t o detect biotin, thus confirming the presence of HIV in the sample.

Example 36
Oligonucleotides with Aminooxy Linkers to Distinguish the Full-length Antisense Oligonucleotide from Deletion Sequences Solid phase synthesis of an oligonucleotide results in a crude product containing not only the desired full-length oligonucleotide (n-length or n-mer), but also multiple, closely-related failure or deletion sequences, primarily of length n−1. These deletion sequences can arise at multiple positions along the oligonucleotide chain. Accordingly, multiple deletion sequences (of length n-1, n-2, n-x) are also present. It is essential to the use of oligonucleotides in various applications to distinguish a full-length sequence from deletion sequences. Aminooxy functionalized oligonucleotides are used to distinguish the full-length oligonucleotide from deletion sequences.

An oligonucleotide (ISIS 2503 complement) of the following sequence is synthesized with an aminooxy linker at the 5'-end using the compound described in Example 3.

5' CCC TGA GGA GCG ATG ACG GAAAAAAAAAAA 3' (SEQ ID NO:9) (polyadenylated tail)

This complement oligonucleotide is then attached to a nylon membrane. Biological fluids containing full-length and deletion sequences are allowed to hybridize with the complement oligonucleotide. Only full-length sequences will bind to the first oligonucleotide, forming complex I. A second oligonucleotide with the following sequence is synthesized:

5' T*TTTT*TTTT*TTTT*TTTT*TTT 3' (SEQ ID NO:10)

5 The *T position has C-5-propargyl-animooxy linker attached to biotin. Complex I is allowed to form a sandwich with the second oligonucleotide. Careful and stringent washing of the sandwich, followed by biotin detection, provides a quantitative method of detecting full-length ISIS 2503.

Example 37
Fluorescence Resonance Energy Transfer (FRET) with Aminooxy Linked Oligonucleotides ISIS 2302 complement sequence of the following sequence is synthesized with extenders at the 5'-end and the 3'-end:

5'-A*AAAATGACGGATGCCAGCTTGGGCTTTTT*-3(SEQ ID NO:11)

At the 3'-end, fluorescein is conjugated via C-5-O—$NH_2$ linker using fluorescamine (Molecular Probes, F-2332, Eugene, Oreg.). At the 5'-end rhodamine is connected using tetramethyl rhodamine isothiocyanate (Molecular Probes, Oreg.) to A via N-6-O—$NH_2$ linker. Fluorescein is a donor dye and rhodamine is an acceptor dye which, when in close proximity to a donor fluorophore, is capable of quenching the fluorescence emitted by the donor fluorophore.

The preferred secondary structure of the oligonucleotide shown above is a stem-and-loop structure wherein the A residues hydridize to the T residues. Upon formation of the stem, fluorescein is positioned in close proximity to rhodamine which allows for energy transfer between the two groups. As a result, the fluorescence emitted by fluorescein is quenched by the acceptor, rhodamine. This is the principle of fluorescence resonance energy transfer (FRET). Binding of a full-length sequence complementary to this oligonucleotide prevents loop formation, thus fluorescence quenching cannot occur. Accordingly, when a full-length oligonucleotide is hybridized to the complement oligonucleotide to form a fully-matched duplex, fluorescence is observed because rhodamine and fluorescein are separated such that rhodamine is incapable of quenching the fluorescence emitted by fluorescein. FRET can be used to distinguish full-length oligonucleotide from deletion sequences, which are oligonucleotides of shorter length formed during oligonucleotide synthesis. To detect presence of a full-length sequence, a stringency wash is employed, which washes away unbound deletion sequences while still allowing the detection of bound full-length oligonucleotide.

Example 38

Aminooxy Oligonucleotides in DNA Arrays for Target Validation

Aminooxy oligonucleotides are introduced into DNA arrays for validating new antisense targets and selecting the best antisense oligonucleotide construct via gene expression profiling.

Fifty antisense oligonucleotides, complementary to different regions of the HDAC gene (Histone deacetylase, Yarden et al., *Proc. Natl. Acad. Sci. USA*, 1999, 96:4938), are synthesized with aminooxy linkers at the 5'-end, using the reagent described in Example 3. These oligonucleotides are attached to a glass slide which has a reactive aldehyde functionality. This DNA array is treated with cells containing the HDAC gene. The target is analyzed for HDAC target gene expression using RT-PCR (as described in Example 39). See, Gibson et al., *Genome Res.*, 1996, 6:995. This procedure allows selection of the best antisense oligonucleotide for the HDAC gene and also validates HDAC for the development of antisense based therapy.

Example 39

Reverse Transcriptase PCR (RT-PCR) of CD40 mRNA Levels

Quantitation of CD40 mRNA levels was determined by reverse transcriptase polymerase chain reaction (RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time.

As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated.

With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents were obtained from PE-Applied Biosystems, Foster City, Calif. RT-PCR reactions were carried out by adding 25 ul PCR cocktail (1×Taqman™ buffer A, 5.5 mM $MgCl_2$, 300 uM each of DATP, dCTP and dGTP, 600 uM of dUTP, 100 nM each of forward primer, reverse primer, and probe, 20 U RNAse inhibitor, 1.25 units AmpliTaq GoldT™, and 12.5 U MuLV reverse transcriptase) to 96 well plates containing 25 ul poly(A) mRNA solution. The RT reaction was carried out by incubation for 30 minutes at 48° C. following a 10 minute incubation at 95° C. to activate the AmpliTaq Gold™, 40 cycles of a two-step PCR protocol were carried out: 95° C. for 15 seconds (denaturation) followed by 60° C. for 1.5 minutes (annealing/extension).

For CD40, the PCR primers were:
forward primer: CAGAGTTCACTGAAACGGAATGC (SEQ ID NO:12),
reverse primer: GGTGGCAGTGTGTCTCTCTGTTC (SEQ ID NO:13),
and the PCR probe was: FAM-TTCCTTGCGGT-GAAAGCGAATTCCT-TAMRA (SEQ ID NO:14) where FAM (PE-Applied Biosystems, Foster City, Calif.) is the fluorescent reporter dye and TAMRA (PE-Applied Biosystems, Foster City, Calif.) is the quencher dye.

For GAPDH the PCR primers were:
forward primer: GAAGGTGAAGGTCGGAGTC (SEQ ID NO:15)
reverse primer: GAAGATGGTGATGGGATTTC (SEQ ID NO:16), and the
PCR probe was: 5' JOE-CAAGCTTCCCGTTCTCAGCC-TAMRA 3' (SEQ ID NO:17) where JOE (PE-Applied Biosystems, Foster City, Calif.) is the fluorescent reporter dye and TAMRA (PE-Applied Biosystems, Foster City, Calif.) is the quencher dye.

Example 40

Aminooxy Oligonucleotides in DNA Arrays for Determining Accessibility of a Target (Southern Assay)

This assay enables discovering antisense reagents by hybridization of RNA to aminooxy functionalized oligonucleotide arrays. See, Southern et al., "Oligonucleotides as Therapeutic Agents," Ciba Foundation Symposium, 1997, 209:38–46.

An array of aminooxy functionalized oligonucleotides (about fifty) complementary to globulin mRNA are synthesized and conjugated to microparticles. Each oligonucleotide is a 20 mer. The oligonucleotide is hybridized with a radioactively-labeled RNA made by transcription of a reverse transcriptase PCR (RT-PCR) product obtained from purified globin mRNA (Gibco BRL Life Technologies, Gaithersberg, Md.) with a T7 promoter incorporated in one of the primers (5'-primer) $^{33}$P is included in the transcription mixture. The transcript, in hybridization buffer (1M NaCl 10 MM Tris pH 8.0, 1 MM EDTA, 0.01% SDS), is applied to the glass plate and hybridization is carried out overnight. After rinsing and washing, the array is exposed to a storage phosphor screen for 20 hours and the screen is scanned in a PhosphorImager. Developed images indicate the best antisense constructs.

Example 41

Aminooxy Oligonucleotides in DNA Arrays for Evaluating Downstream Effects of Antisense Oligonucleotides Five antisense oligonucleotides are synthesized for each c-raf and JNK-2 targets with aminooxy linkers. These are attached to glass slides. Nearly 1000 bp cDNA's are produced by PCR using gene specific primers and plasmid templates containing the full-length cDNA for both genes. PCR products are gel purified. The oligonucleotides on the glass plate are hybridized with $^{32}$P-labeled c-raf. These were then hybridized against total RNA from cells. Analysis of c-raf and JNK-2 messages indicate that c-raf inhibition also affects JNK-2 expression.

Example 42

Conjugation of Aminooxy Oligonucleotides to Contrast Agents

Figure 13:
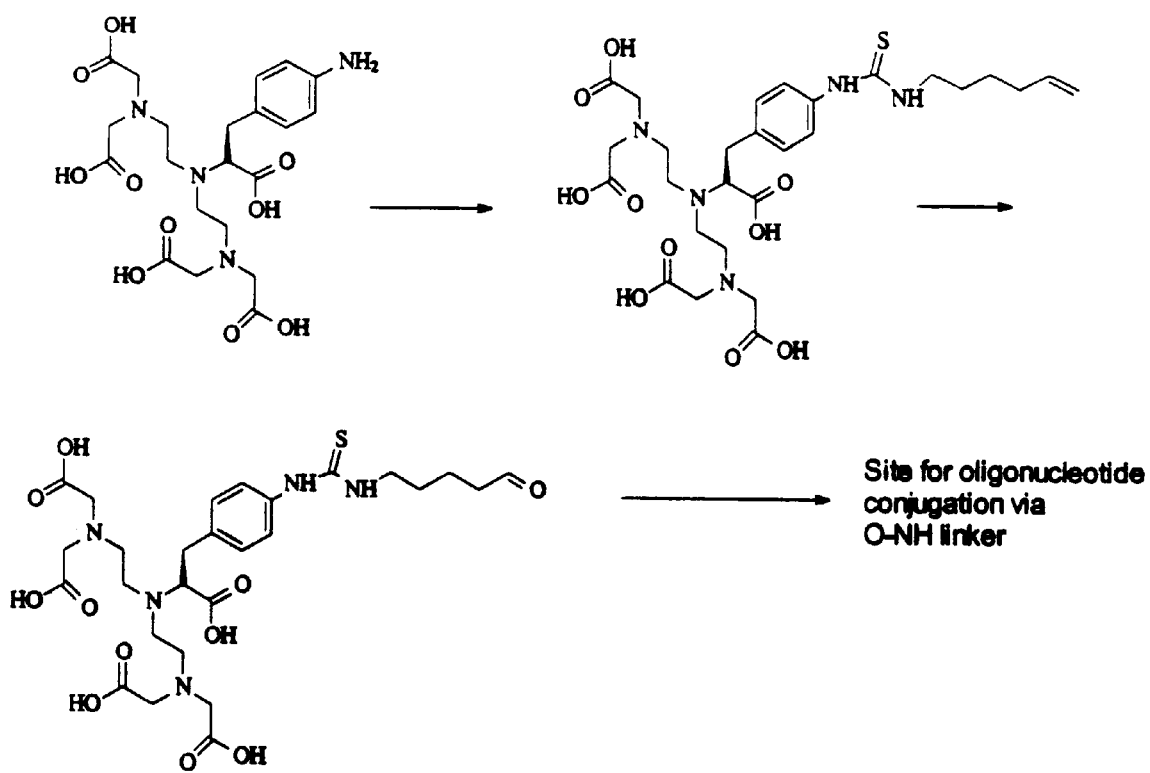
FIG. 13 is a schematic showing the synthesis of an aminooxy linker for conjugation to an oligonucleotide.
Figure 14:
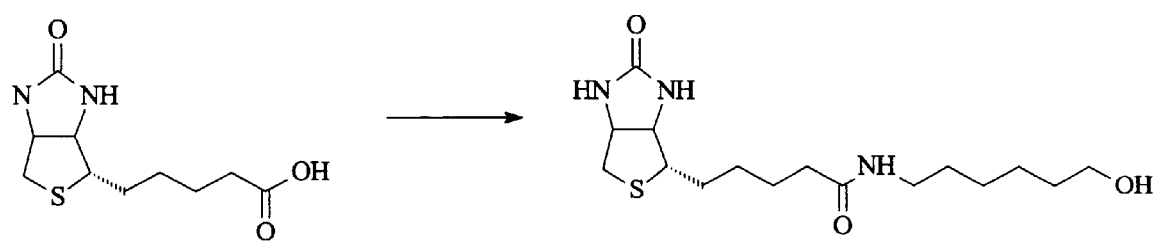
FIG. 14 is a schematic showing the synthesis of a biotin-aminohexanal conjugate.

The DTPA analog shown in FIG. 13 (Williams and Rapoport, *J. Org. Chem.*, 1993, 58:1151) is attached to hexene-1-isothiocyanate and complexed to $Eu^{3+}$ (Lemieux et al., *J. Am. Chem. Soc.*, 1999, 121:4278). The olefinic tether is treated with $OsO_4$/NMM, followed by $NalO_4$, to give the corresponding aldehyde. This aldehyde is conjugated to oligonucleotides targeting cancer cells to localize the tumor sites.

Following is the sequence of a 2'-deoxy phosphorothioate oligonucleotide conjugated to the contrast agent via an aminooxy linkage:

5'TCC GTC ATC GTC ATC GCT CCT CAG GG3'(SEQ ID NO:18)

The contrast agent is attached to the 5' end of the oligonucleotide via an aminooxy linkage. This oligonucleotide is complementary to the H-ras gene.

What is claimed is:

1. An oligonucleotide comprising a plurality of nucleotide units of the structure:

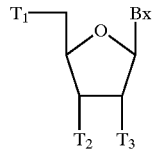

wherein:

Bx is a radical derived from a naturally occurring or non-naturally occurring purine or pyrimidine nucleobase;

each $T_1$ and $T_2$ is, individually, OH, a protected hydroxyl, a nucleotide, a nucleoside or an oligonucleotide;

$T_3$ is H, OH, a protected hydroxyl or a sugar substituent group;

said oligonucleotide further comprising at least one group, R, therein; said R group occurring at the 5'-end, the 3'-end, in lieu of at least one $T_3$ or as a substituent attached to at least one Bx; said R group having one of the formulas:

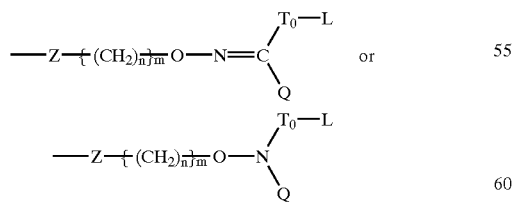

wherein:

each Z is, independently, a single bond, O or a phosphate diester;

each Q is, independently, H, $C_1$–$C_{10}$ alkyl or a nitrogen protecting group;

each $T_0$ is, independently, a bond or a linking moiety, said linking moiety being selected from the group consisting of —O—, —NH—, —S—, substituted or unsubstituted $C_1$–$C_{10}$ alkylenyl, substituted or unsubstituted $C_2$–$C_{10}$ alkenylenyl and substituted or unsubstituted $C_2$–$C_{10}$ alkynylenyl wherein the substituent groups are selected from hydroxyl, alkoxy, benzyl, phenyl, nitro, —SH, —S—$R_{10}$, a halogen atom, alkyl, aryl, alkenyl, alkynyl, and $R_9$—OH, where $R_9$ is alkylenyl, alkenylenyl or alkynylenyl and $R_{10}$ is alkyl, alkenyl, or alkynyl;

each L is, independently, a chemical functional group, a conjugate group or a solid support material, wherein:

said chemical functional group is selected from the group consisting of $C_1$–$C_{10}$ alkyl, substituted $C_1$–$C_{10}$ alkyl, $C_2$–$C_{25}$ alkenyl, substituted $C_2$–$C_{25}$ alkenyl, $C_2$–$C_{15}$ alkynyl, substituted $C_2$–$C_{15}$ alkynyl, $C_4$–$C_7$ carbocyclic alkyl, substituted carbocyclic alkyl, alkenyl carbocyclic, substituted alkenyl carbocyclic, alkynyl carbocyclic, substituted alkynyl carbocyclic, $C_6$–$C_{20}$ aryl, substituted $C_6$–$C_{20}$ aryl, heteroaryl, substituted heteroaryl, a nitrogen, oxygen, or sulfur containing heterocycle group, a substituted nitrogen, oxygen, or sulfur containing heterocycle group, a mixed heterocycle group, or a substituted mixed heterocycle group, where said substituent groups are selected from alkyl, alkenyl, alkynyl, aryl, hydroxyl, alkoxy, $R_9$—OH, benzyl, nitro, —SH, alkoxy-SH, and a halogen atom; or L is phthalimido, an ether group having 2 to 10 carbon atoms and 1 to 4 oxygen or sulfur atoms, a metal coordination group, a halogen atom, hydroxyl, —SH, carboxyl, $NR^{11}R^{12}$, $CONR^{11}$, $C(=NH)NR^{12}R^{13}$, $NHC(=NH)NR^{12}R^{13}$), glutamyl ($R^{11}OOCCH(NR^{12}R^{13})$ $(CH_2)_2C(=O)$, —$NO_3$, —$NO_2$, —CN, trifluoromethyl, trifluoromethoxy, —NH-alkyl, —N-dialkyl, —O-aralkyl, —S-aralkyl, —NH-aralkyl, —$N_3$, —$NHNH_2$, —$ONH_2$, a nucleosidic base, an amino acid side chain, or a carbohydrate, wherein each $R^{11}$ and $R^{12}$ is, independently, H, haloalkyl, $C_1$–$C_{10}$ alkyl, $C_2$–$C_{10}$ alkenyl, $C_2$–$C_{10}$ alkynyl, or $C_6$–$C_{14}$ aryl; and each $R^{13}$ is, independently, $C_6$–$C_{14}$ aryl, substituted $C_6$–$C_{14}$ aryl, heteroaryl, substituted heteroaryl, a nitrogen, oxygen, or sulfur containing heterocycle group, a substituted nitrogen, oxygen, or sulfur containing heterocycle group, a mixed heterocycle group, or a substituted mixed heterocycle group, wherein said substituent groups are selected from hydroxyl, alkoxy, $R_9$—OH, benzyl, phenyl, $NO_2$, SH, alkoxy-SH, a halogen atom, alkyl, aryl, alkenyl, and alkynyl groups;

said conjugate group is selected from the group consisting of radicals derived from an intercalator, a reporter molecule, a contrast reagent, a cleaving agent, a cell targeting agent, a polyether, a phospholipid, cholesterol, acridine, fluorescein, rhodamine, coumarin, pyrene, retinal, a cyanine dye, a polyamine or a polyamide; or Q, $T_0$ and L, together, are a chemical functional group;

each m is, independently, an integer from 1 to about 10; and each n is, independently, an integer from 1 to about 6.

2. The compound of claim 1 wherein at least one L is a conjugate group.

3. The compound of claim 2 wherein said conjugate group is a radical derived from a contrast reagent, a cleaving agent, a cell targeting agent, polyethylene glycol, cholesterol, phospholipid, biotin, phenanthroline, phenazine, phenanthridine, anthra-quinone, acridine, fluorescein, rhodamine, coumarin, pyrene, retinal or a cyanine dye.

4. The compound of claim 2 wherein said conjugate group is attached to said compound via a linking moiety.

5. The compound of claim 1 wherein at least one L is a solid support material.

6. The compound of claim 5 wherein said solid support material is CPG.

7. The compound of claim 5 wherein said solid support material is microparticles.

8. The compound of claim 1 wherein at least one Q, $T_0$ and L, together, are a chemical functional group.

9. The compound of claim 8 wherein said chemical functional group is a retinolyl group.

10. The compound of claim 8 wherein said chemical functional group is a pyrenyl group.

11. The compound of claim 1 wherein Bx is Bx-R.

12. The compound of claim 11 wherein Bx is a radical derived from a purine nucleobase and R is covalently bound to the exocyclic amino functionality at position 6 of said purine nucleobase.

13. The compound of claim 11 wherein R is bound to an exocyclic amino functionality of Bx.

14. The compound of claim 11 wherein R is bound to a cyclic carbon atom of Bx.

15. The compound of claim 11 wherein Bx is 9-adeninyl, 9-(2-amino)adeninyl, or 9-guaninyl.

16. The compound of claim 11 wherein Bx is a radical derived from a pyrimidine nucleobase and R is covalently bound to C5 of Bx.

17. The compound of claim 11 wherein Bx is a radical derived from a pyrimidine, nucleobase and R is covalently bound to the exocyclic amino functionality at position 4 of said pyrimidine nucleobase.

18. The compound of claim 11 wherein Bx is a radical derived from a purine nucleobase and R is covalently bound to the exocyclic amino functionality at position 2 of said purine nucleobase.

* * * * *

UNITED STATES PATENT AND TRADEMARK OFFICE
CERTIFICATE OF CORRECTION

PATENT NO.   : 6,576,752 B1
DATED        : June 10, 2003
INVENTOR(S)  : Muthiah Manoharan et al.

It is certified that error appears in the above-identified patent and that said Letters Patent is hereby corrected as shown below:

<u>Title page,</u>
Item [56], References Cited, FOREIGN PATENT DOCUMENTS, "WO 91/06556" reference, please delete "6/1991" and insert therefor -- 5/1991 --;
OTHER PUBLICATIONS,
"Kozal, M.J. et al.," reference, please delete "Extensivie" and insert therefor
-- Extensive --;
"Kwoh, D.Y. et al.," reference, please delete "Acac." and insert therefor -- Acad --;
"Mukkala, V-M. et al.," reference, please delete "2,2`:6`2" and insert therefor
-- 2,2`:6`,2 --;
"O'Donnell, M.J. et al.," reference, please delete "Malde-TOF" and insert therefor
-- MALDI-TOF --;
"Ouche, T. et al.," reference, please delete "Poly(Ethylene Glycols)s" and insert therefor
-- Poly(Ethylene Glycol)s --;
"Polushin, N.N. et al.," reference, please insert -- - -- between "2" and "Amino";
"Tang, K. et al.," reference, please delete "ionizaiton" and insert therefor
-- ionization --;
"Timofeer, E.N. et al.," reference, please delete "immobilizaiton" and insert therefor
-- immobilization --;
"Hobbs, J. et al.," reference, please insert -- - -- between "2" and "Chloro";
"Ikehara, M. et al.," reference, please delete "2`-bromo-2`deoxyadenylic acid" and insert therefor -- 2`-bromo-2`deoxyadenylic acid --;
"Fahy, E. et al.," reference, please delete "diagnosis" and insert therefor
-- diagnostics --;
"Gibson, U.E.M. et al.," reference, please delete "Quantitive" and insert therefor
-- Quantitative --;

Signed and Sealed this

First Day of June, 2004

JON W. DUDAS
*Acting Director of the United States Patent and Trademark Office*

SEQUENCE LISTING

<160> NUMBER OF SEQ ID NOS: 18

<210> SEQ ID NO 1
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 1
acaccaaaga tgatat                                                      16

<210> SEQ ID NO 2
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 2
acaccaaaga tgatatct                                                    18

<210> SEQ ID NO 3
<211> LENGTH: 21
<212> TYPE: DNA
<213> ORGANISM: Artificial Sequence
<220> FEATURE:
<221> NAME/KEY: misc_feature
<223> OTHER INFORMATION: Novel Sequence
<221> NAME/KEY: misc_feature
<222> LOCATION: (1)..(5)
<223> OTHER INFORMATION: N4- (6-aminohexyl)-2'-deoxycytidine

<400> SEQUENCE: 3
nnnnnatatc atctttggtg t                                                21

<210> SEQ ID NO 4
<211> LENGTH: 21
<212> TYPE: DNA
<213> ORGANISM: Artificial Sequence

```
<220> FEATURE:
<221> NAME/KEY: misc_feature
<223> OTHER INFORMATION: Novel Sequence
<221> NAME/KEY: misc_feature
<222> LOCATION: (1)..(5)
<223> OTHER INFORMATION: N4- (6-aminohexyl)-2'-deoxycytidine

<400> SEQUENCE: 4
nnnnntcatg agtcaagtct a                                          21

<210> SEQ ID NO 5
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 5
tctgagtagc agaggagctc                                            20

<210> SEQ ID NO 6
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 6
tccgtcatcg ctcctcaggg                                            20

<210> SEQ ID NO 7
<211> LENGTH: 26
<212> TYPE: DNA
<213> ORGANISM: Human immunodeficiency virus

<400> SEQUENCE: 7
gccagagagc tcccaggctc agatct                                     26

<210> SEQ ID NO 8
<211> LENGTH: 19
<212> TYPE: DNA
<213> ORGANISM: Human immunodeficiency virus

<400> SEQUENCE: 8
ggtctaacca cagagaccc                                             19

<210> SEQ ID NO 9
<211> LENGTH: 30
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 9
ccctgaggag cgatgacgga aaaaaaaaaa                                 30

<210> SEQ ID NO 10
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence
```

<400> SEQUENCE: 10
tttttttttt tttttttttt                                              20

<210> SEQ ID NO 11
<211> LENGTH: 30
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 11
aaaaatgacg gatgccagct gggcttttt                                    30

<210> SEQ ID NO 12
<211> LENGTH: 23
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 12
cagagttcac tgaaacggaa tgc                                          23

<210> SEQ ID NO 13
<211> LENGTH: 23
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 13
ggtggcagtg tgtctctctg ttc                                          23

<210> SEQ ID NO 14
<211> LENGTH: 25
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 14
ttccttgcgg tgaaagcgaa ttcct                                        25

<210> SEQ ID NO 15
<211> LENGTH: 19
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 15
gaaggtgaag gtcggagtc                                               19

<210> SEQ ID NO 16
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 16

```
gaagatggtg atgggatttc                                            20

<210> SEQ ID NO 17
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 17
caagcttccc gttctcagcc                                            20

<210> SEQ ID NO 18
<211> LENGTH: 26
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 18
tccgtcatcg tcatcgctcc tcaggg                                     26
```